United States Patent [19]
Saras et al.

[11] Patent Number: 6,083,721
[45] Date of Patent: Jul. 4, 2000

[54] ISOLATED NUCLEIC ACID MOLECULES ENCODING PARG, A GTPASE ACTIVATING PROTEIN WHICH INTERACTS WITH PTPL1

[75] Inventors: Jan Saras; Petra Franzén; Pontus Aspenström; Ulf Hellman, all of Uppsala, Sweden; Leonel Jorge Gonez, Hughesdale, Australia; Carl-Henrik Heldin, Uppsala, Sweden

[73] Assignee: Ludwig Institute for Cancer Research, New York, N.Y.

[21] Appl. No.: 09/080,855

[22] Filed: May 18, 1998

Related U.S. Application Data

[63] Continuation-in-part of application No. 08/805,583, Feb. 25, 1997, abandoned.

[51] Int. Cl.$^7$ .............................. C12P 21/02; C12P 19/34; C07H 21/00; C12N 1/00; C12N 5/10

[52] U.S. Cl. .................. 435/69.1; 435/91.1; 435/243; 435/320.1; 435/325; 435/410; 536/23.1; 536/23.5; 536/24.31; 536/24.33

[58] Field of Search .................. 536/23.1, 23.5, 536/24.3, 24.31, 24.33; 435/320.1, 325, 410, 243, 69.1, 91.1

[56] References Cited

U.S. PATENT DOCUMENTS

Re. 35,171  3/1996  McCormick et al. ................. 530/350

FOREIGN PATENT DOCUMENTS

WO 94/16069  7/1994  WIPO .
WO 95/06735  3/1995  WIPO .
WO95/06735   9/1995  WIPO .

OTHER PUBLICATIONS

Ach et al, PNAS (USA), vol. 91: pp. 5863–5867, Jun. 1994.
Wilson et al, Nature, vol. 368: pp. 32–38, Mar. 1994.
Ngo et al, The protein Folding Problem and Tertiary Structure Prediction, Mertz et al (eds.), Birkhauser, Boston, pp. 433 and 492–495, 1994.
Saras and Heldin, *TIBS Trends in Biochemical Sciences* 21:455–458 (1996).
Lamarche and Hall, *Trends in Genetics* 10:436–440 (1994).
Diekmann and Hall, *Methods in Enzymology* 256:207–215 (1995).
Price et al., *Curr. Biol.* 5:68–73 (1995).
EMBL database entry EMEST7:HS763831, Accession No. L49573 (1995).
EMBL database entry EMEST6:HS49515, Accession No. T32495 (1995).
EMBL database entry EMEST10:HSC19G091, Accession No. Z43348 (1994).
Saras et al., *The Journal of Biological Chemistry* 272:24333–24338 (1997).
Symons, *Current Opinion in Biotechnology* 6:668–674 (1995).
White et al., *Biochemical and Biophysical Research Communications* 227:118–224 (1996).
Aspenström and Olson, *Methods in Enzymology* 256:228–241 (1995).
Boguski and McCormick, *Nature* 366:643–654 (1993).
Lamarche and Hall, Trends Genet. 10:436–440, 1994.
Lancaster et al., J. Biol. Chem. 269:1137–1142, 1994.
Reinhard et al., EMBO J. 14:697–704, 1995.
Settleman et al., Nature 359:153–154, 1992.
Homma and Emori, EMBO J. 14:286–291, 1995.
Sato et al., Science 268:411–415, 1995.
Ponting and Phillips, Trends Biochem. Sci. 20:102–103, 1995.
Wilson et al., Nature 368:32–38, 1994.
Newton, Curr. Biol. 5:973–976, 1995.
Ahmed et al., Biochem J. 280:233–241, 1991.
Ono et al., Proc. Natl. Acad. Sci. USA 86:4868–4871, 1989.
Ahmed et al., J. Biol. Chem. 268:10709–10712, 1993.

*Primary Examiner*—Terry McKelvey
*Attorney, Agent, or Firm*—Wolf, Greenfield & Sacks, P.C.

[57] ABSTRACT

The invention describes nucleic acids encoding the PARG protein, including fragments and biologically functional variants thereof. Also included are polypeptides and fragments thereof encoded by such nucleic acids, and antibodies relating thereto. Methods and products for using such nucleic acids and polypeptides also are provided.

24 Claims, 10 Drawing Sheets

```
MIAHKQKKTKKKRAWASGQLSTDITTSEMGLKSLSLSSNSIFDPDYIKELVNDIRKFSHILLYLKEAIFSDCFKEVIHRLE      80
ELLRVLKSIMNKHQNLNSVDLQNAAEMLTAKVKAVNFTEVNEENKNDLFQEVFSSIETLAFTFGNILTNFLMGDVGNDSF     160
LRLPVSRETKSFENVSVESVDSSSEKGNFSPLELDNVLKNTDSIELALSYAKTWSKYTKNIVSWVEKKLNLELESTRNM     240
VKLAEATRTNIGIQEFMPLQSLFTNALLNDIESSHLLQQTIAALQANKFVQPLLGRKNEMEKQRKEIKELWKQEQNKMLE     320
AENALKKAKLLCMQRQDEYEKAKSSMFRAEEEHLSSSGLAKNLNKQLEKKRRLEEEALQKVEEADELYKVCVTNVEERR     400
NDVENTKREILAQLRTLVFQCDLTLKAVTVNLFHMQHLQAASLADRLQSLCGSAKLYDPGQEYSEFVKATNSTEEEKVDG     480
NVNKHLNSSQPSGFGPANSLEDVVRLPDSSNKIEEDRCSNSADITGPSFIRSWTFGMFSDSESTGGSSESRSLDSESISP     560
GDFHRKLPRTPSSGTMSSADDLEREPPSPSETGPNSLGTFKKTLMSKAALTHKFRKLRSPTKCRDCEGIVVFQGVECEE     640
CLLVCHRKCLENLVIICGHQKLPGKIHLFGAEFTLVAKKEPDGIPFILKICASEIENRALCLQGIYRVCGNKIKTEKLCL     720
ALENGMHLVDISEFSSHDICDVLKLYLRQLPEPFILFRLYKEFIDLAKEIQHVNEEQETKKNSLEDKKWPNMCIEINRIL    800
LKSKDLLRQLPASNFNSLHFLIVHLKRVVDHAEENKMNSKNLGVIFGPSLIRPRPQTAPITISSLAEYSNQARLVEFLIT    880
YSQKIFDGSLQPQDVMCSIGVVDQGCFPKPLLSPEERDIERSMKSLFFSSKEDIHTSESESKIFERATSFEESERKQNAL    960
GKCDACLSDKAQLLLDQEAESASQKIEDGKAPKPLSLKSDRSTNNVERHTPRTKIRPVSLPVDRLLLASPPNERNGRNMG   1040
NVNLDKFCKNPAFEGVNRKDAATTVCSKFNGFDQQTLQKIQDKQYEQNSLTAKTTMIMPSALQEKGVTTSLQISGDHSIN   1120
ATQPSKPYAEPVRSVREASERRSSDSYPLAPVRAPRTLQPQHWTTFYKPHAPIISIRGNEEKPASPSAACPPGTDHDPHG   1200
LVVKSMPDDKASACPGQATGQPKEDSEELGLPDVNPMCQRPRLKRMQQFEDLEDEIPQFV   1261
```

FIG. 3A

```
ELDNVLLKNTDSIELALSYAKTWSKYTKNIVSWVEKKLNL     PARG
EHDKLLISRTDGVDVAFERTKAWSTYSKDVISYVRARIQL    ZK669.1a

LESTRNMVKLAEATRTNIGIQEFMPLQSLFTNALLNDIE      PARG
EQDHARKVHTLVDTSRRDH-KPFMPLREIFENSFDTEVE     ZK669.1a

SSHLLQQTIAALQANKFVQPLLGRKNEMEKQRKEIKELWK     PARG.
MVTHTKETTEHLK-DRVVEALDARRKEHDTVRNALKVEWT    ZK669.1a

-----QEQNKMLEAENALKKAKLLCMQRQDE-             PARG.
KATKSLHDCEESYEKSKITLRMREEALKKARESCLRTES-    ZK669.1a

YEKAKSSMFRAEEEHLSSGGLAKNLNKQLEKKRLEEEA       PARG
-------SPPEREASRRRDLEKKSRAVEEA              ZK669.1a

LQKVEEADELYKVCVTNVEERRNDVENTKREILAQLRTLV     PARG
MIKKEAERQVVSITAELRKKRDIDKTKESVVERLRELI      ZK669.1a

FQCDLTLKAVTVNLFHMQHLQAASLADRLQSLCGSAKLYD     PARG
FQCEQTTKACTVHYFTSLAALWALPGAFHELSNATRDYQ     ZK669.1a

PGQEYSEFV---KATNSTEEKVDGNVNKHLNSSQ-PS        PARG
PGTEYMAFLQTLPTRAASSLVRSDRSIDEGVASCDGSS      ZK669.1a

GFGP---ANSLEDVVRLPDS                         PARG
SLTSLRRNAINPDDEGALPDT                       ZK669.1a
```

FIG. 3B

PARG

ZK669.1a

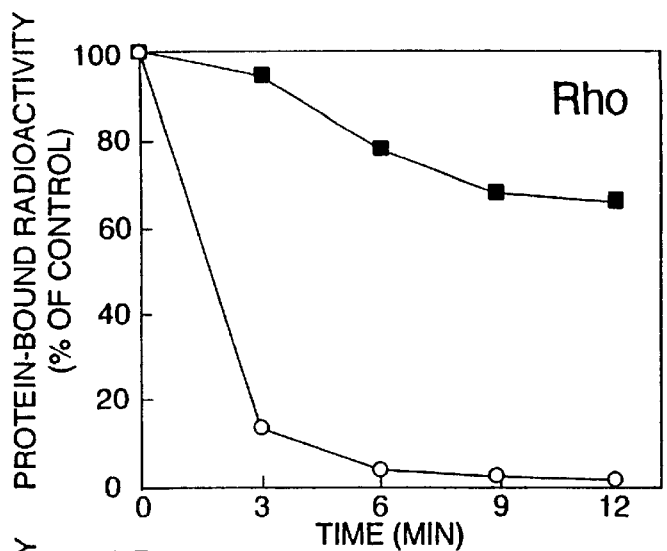
FIG. 5B
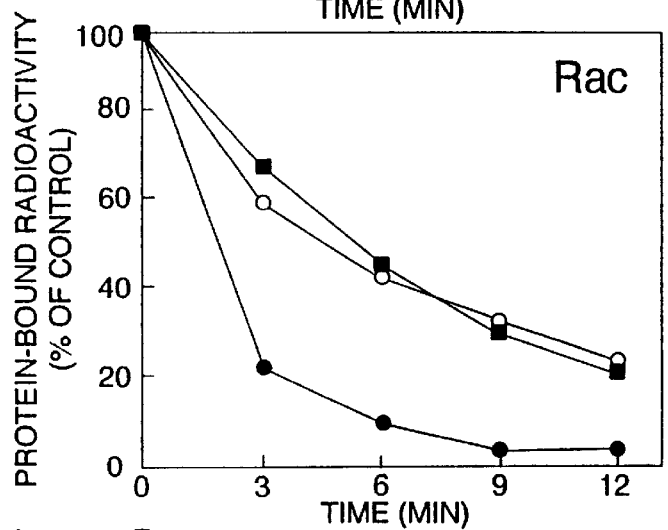
FIG. 5C
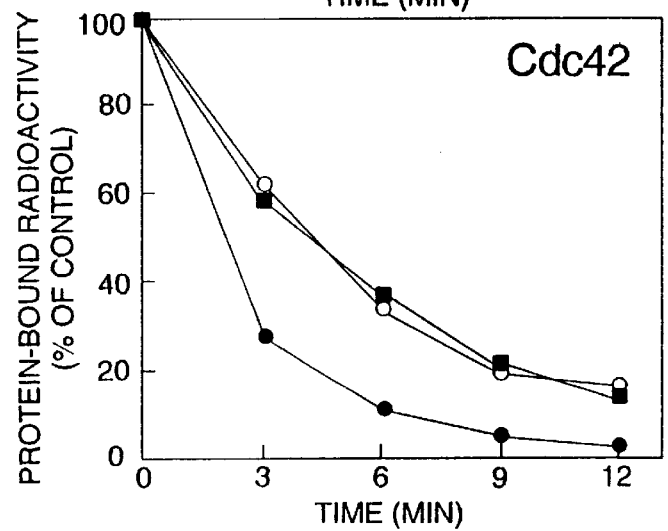
FIG. 5D
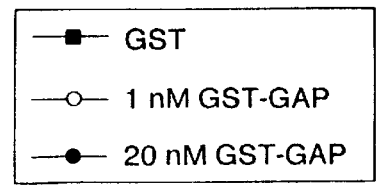

SEQUENCE LISTING

```
<160> NUMBER OF SEQ ID NOS: 39

<210> SEQ ID NO 1
<211> LENGTH: 5238
<212> TYPE: DNA
<213> ORGANISM: Homo sapiens
<220> FEATURE:
<221> NAME/KEY: CDS
<222> LOCATION: 184..3966

<400> SEQUENCE: 1
gctgtggctg cggctgcggc tgcggctgag atttggccgg gcgtccgcag gccgtggggg      60 atggggcag cgagctccag ccctcggcgg tggcggcggc cgtaggtgtg gggcgggcgt     120
ccgcgtccgg cacgcgagat ggagcgccgt ggatttcagt ttttctgact gttacatgaa    180 agg atg att gct cac aaa cag aaa aag aca aag aaa aaa cgt gct tgg      228
    Met Ile Ala His Lys Gln Lys Lys Thr Lys Lys Lys Arg Ala Trp
    1               5                   10                  15 gca tca ggt caa ctc tct act gat att aca act tct gaa atg ggg ctc      276
Ala Ser Gly Gln Leu Ser Thr Asp Ile Thr Thr Ser Glu Met Gly Leu
                20                  25                  30 aag tcc tta agt tcc aac tct att ttt gat ccg gat tac atc aag gag      324
Lys Ser Leu Ser Ser Asn Ser Ile Phe Asp Pro Asp Tyr Ile Lys Glu
            35                  40                  45 ttg gtg aat gat atc agg aag ttc tcc cac atc tta cta tat ttg aaa      372
Leu Val Asn Asp Ile Arg Lys Phe Ser His Ile Leu Leu Tyr Leu Lys
        50                  55                  60 gaa gcc ata ttt tca gac tgt ttt aaa gaa gtt att cat ata cgt cta      420
Glu Ala Ile Phe Ser Asp Cys Phe Lys Glu Val Ile His Ile Arg Leu
```

-continued

```
              65                  70                  75
gag gaa ctg ctc cgt gtt tta aag tct ata atg aat aaa cat cag aac      468
Glu Glu Leu Leu Arg Val Leu Lys Ser Ile Met Asn Lys His Gln Asn
 80                  85                  90                  95 ctc aat tct gtt gat ctt caa aat gct gca gaa atg ctc act gca aaa      516
Leu Asn Ser Val Asp Leu Gln Asn Ala Ala Glu Met Leu Thr Ala Lys
                    100                 105                 110 gtg aaa gct gtg aac ttc aca gaa gtt aat gaa gaa aac aaa aac gat      564
Val Lys Ala Val Asn Phe Thr Glu Val Asn Glu Glu Asn Lys Asn Asp
            115                 120                 125 ctc ttc cag gaa gtg ttt tct tct att gaa act ttg gca ttt acc ttt      612
Leu Phe Gln Glu Val Phe Ser Ser Ile Glu Thr Leu Ala Phe Thr Phe
        130                 135                 140 gga aat atc ctt aca aac ttc ctt atg gga gat gta ggc aat gat tca      660
Gly Asn Ile Leu Thr Asn Phe Leu Met Gly Asp Val Gly Asn Asp Ser
    145                 150                 155 ttc ttg cga ctg cct gtt tct cga gaa act aag tcg ttt gaa aat gtt      708
Phe Leu Arg Leu Pro Val Ser Arg Glu Thr Lys Ser Phe Glu Asn Val
160                 165                 170                 175 tct gtg gaa tca gtg gac tca tcc agt gaa aaa gga aat ttt tcc cct      756
Ser Val Glu Ser Val Asp Ser Ser Ser Glu Lys Gly Asn Phe Ser Pro
                    180                 185                 190 tta gaa cta gac aac gtg ctg tta aag aac act gac tct atc gag ctg      804
Leu Glu Leu Asp Asn Val Leu Leu Lys Asn Thr Asp Ser Ile Glu Leu
            195                 200                 205 gct ttg tca tat gct aaa act tgg tca aaa tat act aag aac ata gtt      852
Ala Leu Ser Tyr Ala Lys Thr Trp Ser Lys Tyr Thr Lys Asn Ile Val
        210                 215                 220 tca tgg gtt gaa aaa aag ctt aac ttg gaa ttg gag tcc act aga aat      900
Ser Trp Val Glu Lys Lys Leu Asn Leu Glu Leu Glu Ser Thr Arg Asn
    225                 230                 235 atg gtc aag ttg gca gag gca act aga act aac att gga att cag gag      948
Met Val Lys Leu Ala Glu Ala Thr Arg Thr Asn Ile Gly Ile Gln Glu
240                 245                 250                 255 ttc atg cca ctg cag tct ctg ttt act aat gct ctt ctt aat gat ata      996
Phe Met Pro Leu Gln Ser Leu Phe Thr Asn Ala Leu Leu Asn Asp Ile
                    260                 265                 270 gaa agc agt cac ctt tta caa caa aca att gca gct ctc cag gct aac     1044
Glu Ser Ser His Leu Leu Gln Gln Thr Ile Ala Ala Leu Gln Ala Asn
            275                 280                 285 aaa ttt gtg cag cct cta ctt gga agg aaa aat gaa atg gaa aaa caa     1092
Lys Phe Val Gln Pro Leu Leu Gly Arg Lys Asn Glu Met Glu Lys Gln
        290                 295                 300 agg aaa gaa ata aaa gag ctt tgg aaa cag gag caa aat aaa atg ctt     1140
Arg Lys Glu Ile Lys Glu Leu Trp Lys Gln Glu Gln Asn Lys Met Leu
    305                 310                 315 gaa gca gag aat gct ctc aaa aag gca aaa tta tta tgc atg caa cgt     1188
Glu Ala Glu Asn Ala Leu Lys Lys Ala Lys Leu Leu Cys Met Gln Arg
320                 325                 330                 335 caa gat gaa tat gag aaa gca aag tct tcc atg ttt cgt gca gaa gag     1236
Gln Asp Glu Tyr Glu Lys Ala Lys Ser Ser Met Phe Arg Ala Glu Glu
                    340                 345                 350 gag cat ctg tct tca agt ggc gga tta gca aaa aat ctc aac aag caa     1284
Glu His Leu Ser Ser Ser Gly Gly Leu Ala Lys Asn Leu Asn Lys Gln
            355                 360                 365 cta gaa aaa aag cga agg ttg gaa gag gag gct ctc caa aaa gta gaa     1332
Leu Glu Lys Lys Arg Arg Leu Glu Glu Glu Ala Leu Gln Lys Val Glu
        370                 375                 380 gaa gca gat gaa ctt tac aaa gtt tgt gtg aca aat gtt gaa gaa aga     1380
```

-continued

```
Glu Ala Asp Glu Leu Tyr Lys Val Cys Val Thr Asn Val Glu Glu Arg
            385                 390                 395 aga aat gat gta gaa aat acc aaa aga gaa att tta gca caa ctc cgg       1428
Arg Asn Asp Val Glu Asn Thr Lys Arg Glu Ile Leu Ala Gln Leu Arg
400                 405                 410                 415 aca ctt gtt ttc cag tgt gat ctt acc ctt aaa gcg gta aca gtt aac       1476
Thr Leu Val Phe Gln Cys Asp Leu Thr Leu Lys Ala Val Thr Val Asn
                420                 425                 430 ctc ttc cac atg cag cat ctg cag gct gct tcc ctt gca gac aga tta       1524
Leu Phe His Met Gln His Leu Gln Ala Ala Ser Leu Ala Asp Arg Leu
            435                 440                 445 cag tct ctc tgt ggt agt gcc aaa ctc tat gac cca ggc caa gag tac       1572
Gln Ser Leu Cys Gly Ser Ala Lys Leu Tyr Asp Pro Gly Gln Glu Tyr
        450                 455                 460 agt gaa ttt gtc aag gcc aca aat tca act gaa gaa gaa aaa gtt gat       1620
Ser Glu Phe Val Lys Ala Thr Asn Ser Thr Glu Glu Glu Lys Val Asp
    465                 470                 475 gga aat gta aat aaa cat tta aat agt tcc caa cct tca gga ttt gga       1668
Gly Asn Val Asn Lys His Leu Asn Ser Ser Gln Pro Ser Gly Phe Gly
480                 485                 490                 495 cct gcc aac tct tta gag gat gtt gta cgc ctt cct gac agt tct aat       1716
Pro Ala Asn Ser Leu Glu Asp Val Val Arg Leu Pro Asp Ser Ser Asn
                500                 505                 510 aaa att gaa gag gac aga tgc tct aac agt gca gat ata aca ggt cct       1764
Lys Ile Glu Glu Asp Arg Cys Ser Asn Ser Ala Asp Ile Thr Gly Pro
            515                 520                 525 tcc ttt ata aga tca tgg aca ttt ggg atg ttt agt gat tct gag agc       1812
Ser Phe Ile Arg Ser Trp Thr Phe Gly Met Phe Ser Asp Ser Glu Ser
        530                 535                 540 act gga ggg agc agc gaa tct aga tct ctg gat tca gaa tct ata agt       1860
Thr Gly Gly Ser Ser Glu Ser Arg Ser Leu Asp Ser Glu Ser Ile Ser
    545                 550                 555 cca gga gac ttt cat cga aaa ctt cca cga aca cca tcc agt gga act       1908
Pro Gly Asp Phe His Arg Lys Leu Pro Arg Thr Pro Ser Ser Gly Thr
560                 565                 570                 575 atg tcc tct gca gat gat cta gat gaa aga gag cca cct tcc cct tca       1956
Met Ser Ser Ala Asp Asp Leu Asp Glu Arg Glu Pro Pro Ser Pro Ser
                580                 585                 590 gaa act gga ccc aat tcc ctt gga aca ttt aag aaa aca ttg atg tca       2004
Glu Thr Gly Pro Asn Ser Leu Gly Thr Phe Lys Lys Thr Leu Met Ser
            595                 600                 605 aag gca gct ctc aca cac aag ttt cgc aaa ttg aga tcc ccc acg aaa       2052
Lys Ala Ala Leu Thr His Lys Phe Arg Lys Leu Arg Ser Pro Thr Lys
        610                 615                 620 tgt agg gat tgt gaa ggc att gta gtg ttc caa ggt gtt gaa tgt gaa       2100
Cys Arg Asp Cys Glu Gly Ile Val Val Phe Gln Gly Val Glu Cys Glu
    625                 630                 635 gag tgt ctc ctt gtt tgt cat cga aag tgt ttg gaa aat tta gtc att       2148
Glu Cys Leu Leu Val Cys His Arg Lys Cys Leu Glu Asn Leu Val Ile
640                 645                 650                 655 att tgt ggt cat cag aaa ctt cca gga aaa ata cac tta ttt gga gca       2196
Ile Cys Gly His Gln Lys Leu Pro Gly Lys Ile His Leu Phe Gly Ala
                660                 665                 670 gaa ttc aca cta gtt gca aaa aag gaa cca gat ggt atc cct ttt ata       2244
Glu Phe Thr Leu Val Ala Lys Lys Glu Pro Asp Gly Ile Pro Phe Ile
            675                 680                 685 ctc aaa ata tgt gcc tca gag att gaa aat aga gct ttg tgt cta cag       2292
Leu Lys Ile Cys Ala Ser Glu Ile Glu Asn Arg Ala Leu Cys Leu Gln
        690                 695                 700
```

-continued

```
gga att tat cgt gtg tgt gga aac aaa ata aaa act gaa aaa ttg tgt      2340
Gly Ile Tyr Arg Val Cys Gly Asn Lys Ile Lys Thr Glu Lys Leu Cys
705                 710                 715 cta gct ttg gaa aat ggt atg cac ttg gta gat att tca gaa ttt agt      2388
Leu Ala Leu Glu Asn Gly Met His Leu Val Asp Ile Ser Glu Phe Ser
720                 725                 730                 735 tca cat gat atc tgt gac gtc ttg aaa tta tac ctt cgg cag ctc cca      2436
Ser His Asp Ile Cys Asp Val Leu Lys Leu Tyr Leu Arg Gln Leu Pro
        740                 745                 750 gaa cca ttt att tta ttt cga ttg tac aag gaa ttt ata gac ctt gca      2484
Glu Pro Phe Ile Leu Phe Arg Leu Tyr Lys Glu Phe Ile Asp Leu Ala
    755                 760                 765 aaa gag atc caa cat gta aat gaa gaa caa gag aca aaa aag aat agt      2532
Lys Glu Ile Gln His Val Asn Glu Glu Gln Glu Thr Lys Lys Asn Ser
770                 775                 780 ctt gaa gac aaa aaa tgg cca aat atg tgt ata gaa ata aac cga att      2580
Leu Glu Asp Lys Lys Trp Pro Asn Met Cys Ile Glu Ile Asn Arg Ile
785                 790                 795 ctt cta aaa agc aaa gac ctt cta aga caa ttg cca gca tca aat ttt      2628
Leu Leu Lys Ser Lys Asp Leu Leu Arg Gln Leu Pro Ala Ser Asn Phe
800                 805                 810                 815 aac agt ctt cat ttc ctt ata gta cat cta aag cgg gta gta gat cat      2676
Asn Ser Leu His Phe Leu Ile Val His Leu Lys Arg Val Val Asp His
        820                 825                 830 gca gaa gaa aac aag atg aac tcc aaa aac ttg ggg gtg ata ttt gga      2724
Ala Glu Glu Asn Lys Met Asn Ser Lys Asn Leu Gly Val Ile Phe Gly
    835                 840                 845 cca agt ctc att agg cca agg cca caa act gct cct atc acc atc tcc      2772
Pro Ser Leu Ile Arg Pro Arg Pro Gln Thr Ala Pro Ile Thr Ile Ser
850                 855                 860 tcc ctt gca gag tat tca aat caa gca cgc ttg gta gag ttt ctc att      2820
Ser Leu Ala Glu Tyr Ser Asn Gln Ala Arg Leu Val Glu Phe Leu Ile
865                 870                 875 act tac tca cag aag atc ttc gat ggg tcc cta caa cca caa gat gtt      2868
Thr Tyr Ser Gln Lys Ile Phe Asp Gly Ser Leu Gln Pro Gln Asp Val
880                 885                 890                 895 atg tgt agc ata ggt gtt gtt gat caa ggc tgt ttt cca aag cct ctg      2916
Met Cys Ser Ile Gly Val Val Asp Gln Gly Cys Phe Pro Lys Pro Leu
        900                 905                 910 tta tca cca gaa gaa aga gac att gaa cgt tcc atg aag tca cta ttt      2964
Leu Ser Pro Glu Glu Arg Asp Ile Glu Arg Ser Met Lys Ser Leu Phe
    915                 920                 925 ttt tct tca aag gaa gat atc cat act tca gag agt gaa agc aaa att      3012
Phe Ser Ser Lys Glu Asp Ile His Thr Ser Glu Ser Glu Ser Lys Ile
930                 935                 940 ttt gaa cga gct aca tca ttt gag gaa tca gaa cgc aag caa aat gcg      3060
Phe Glu Arg Ala Thr Ser Phe Glu Glu Ser Glu Arg Lys Gln Asn Ala
945                 950                 955 tta gga aaa tgt gat gca tgt ctc agt gac aaa gca cag ttg ctt cta      3108
Leu Gly Lys Cys Asp Ala Cys Leu Ser Asp Lys Ala Gln Leu Leu Leu
960                 965                 970                 975 gac caa gag gct gaa tca gca tcc caa aag ata gaa gat ggt aaa gcc      3156
Asp Gln Glu Ala Glu Ser Ala Ser Gln Lys Ile Glu Asp Gly Lys Ala
        980                 985                 990 cct aag cca ctt tct ctg aaa tct gat agg tca aca aac aat gtg gag      3204
Pro Lys Pro Leu Ser Leu Lys Ser Asp Arg Ser Thr Asn Asn Val Glu
    995                 1000                1005 agg cat act cca agg acc aag att aga cct gta agt ttg cct gta gat      3252
Arg His Thr Pro Arg Thr Lys Ile Arg Pro Val Ser Leu Pro Val Asp
1010                1015                1020
```

-continued

```
aga cta ctt ctt gca agt cct cct aat gag aga aat ggc aga aat atg        3300
Arg Leu Leu Leu Ala Ser Pro Pro Asn Glu Arg Asn Gly Arg Asn Met
    1025                1030                1035 gga aat gta aat tta gac aag ttt tgc aag aat cct gcc ttt gaa gga        3348
Gly Asn Val Asn Leu Asp Lys Phe Cys Lys Asn Pro Ala Phe Glu Gly
1040                1045                1050                1055 gtt aat aga aaa gac gct gct act act gtt tgt tcc aaa ttt aat ggc        3396
Val Asn Arg Lys Asp Ala Ala Thr Thr Val Cys Ser Lys Phe Asn Gly
                1060                1065                1070 ttt gac cag caa act cta cag aaa att cag gac aaa cag tat gaa caa        3444
Phe Asp Gln Gln Thr Leu Gln Lys Ile Gln Asp Lys Gln Tyr Glu Gln
            1075                1080                1085 aac agc cta act gcc aag act aca atg atc atg ccc agt gca ctc cag        3492
Asn Ser Leu Thr Ala Lys Thr Thr Met Ile Met Pro Ser Ala Leu Gln
        1090                1095                1100 gaa aaa gga gtg aca aca agc ctc cag att agt ggg gac cat tct atc        3540
Glu Lys Gly Val Thr Thr Ser Leu Gln Ile Ser Gly Asp His Ser Ile
    1105                1110                1115 aat gcc act caa ccc agt aag cca tat gca gag cca gtc agg tca gtg        3588
Asn Ala Thr Gln Pro Ser Lys Pro Tyr Ala Glu Pro Val Arg Ser Val
1120                1125                1130                1135 aga gag gca tct gag aga cgg tct tca gat tcc tac cct ctc gct cct        3636
Arg Glu Ala Ser Glu Arg Arg Ser Ser Asp Ser Tyr Pro Leu Ala Pro
                1140                1145                1150 gtc aga gca ccc aga aca ctg cag cct caa cat tgg aca aca ttt tat        3684
Val Arg Ala Pro Arg Thr Leu Gln Pro Gln His Trp Thr Thr Phe Tyr
            1155                1160                1165 aaa cca cat gct ccc atc atc agt atc agg ggg aat gag gag aag cca        3732
Lys Pro His Ala Pro Ile Ile Ser Ile Arg Gly Asn Glu Glu Lys Pro
        1170                1175                1180 gct tca ccc tca gca gca tgc cct cct ggc aca gat cac gat ccc cac        3780
Ala Ser Pro Ser Ala Ala Cys Pro Pro Gly Thr Asp His Asp Pro His
    1185                1190                1195 ggt ctc gtg gtg aag tca atg cca gac cca gac aaa gca tca gct tgt        3828
Gly Leu Val Val Lys Ser Met Pro Asp Pro Asp Lys Ala Ser Ala Cys
1200                1205                1210                1215 cct ggg caa gca act ggt caa cct aaa gaa gac tct gag gag ctt ggc        3876
Pro Gly Gln Ala Thr Gly Gln Pro Lys Glu Asp Ser Glu Glu Leu Gly
                1220                1225                1230 ttg cct gat gtg aat cca atg tgt cag aga cca agg cta aaa cga atg        3924
Leu Pro Asp Val Asn Pro Met Cys Gln Arg Pro Arg Leu Lys Arg Met
            1235                1240                1245 caa cag ttt gaa gac ctc gaa gat gaa att cca caa ttt gtg                3966
Gln Gln Phe Glu Asp Leu Glu Asp Glu Ile Pro Gln Phe Val
        1250                1255                1260 tagggatgtc aaatttcagg gttttttgt tgttgttgtg ttattttgtg gtattgtgct       4026
tgttttgtga aagaatgttt tgacagggcc cctttttgtat aggactgcca aatcatgggt    4086 tttgccttt gttgttgtat ttatcctctg ttggtaatac tgaatggtag aatgttttga      4146
tagggtcaca tttgtgcctc actggaatta tctttaaatt ctgtattttt aaagttgtga     4206
ataagatagg tggattcgta ttttttaaag ttcagttgac tttccccacc aaatggtcca     4266
tttgaatgca tccctaatat atgatatagt ctcaactaat aggtgcaatt tgggaaaatc     4326
aggtttattt tttggagtgg aactgttata agtgcttatt tataaaagga atgtttctga     4386
atgcaagtgc ctaaaaagat ctttgttggt atgcatatgt tttgtcacac aatttatagt     4446
gcatctttca ccatttgtgc ttttttaaga tagtatgtaa gctcttattt ttcaattggc     4506
```

-continued

```
aattcagtta attttttaaat gtttacataa tggccagaag gcttgcaaat ctgtatttaa    4566
ttgcatttta attaattgcc agtttttaca tgtagtagtc agttgtacaa agaaaatgca    4626
cttaaacctg tttctaaatt atatattcag ttatattata tttggcttta gatggtttta    4686
atacatttga tagttttca cccttggct ttattttata taaacttttg ttttcagca       4746 gttctgaact ttttagtatt ttataaatgg tccaaaaaat gcctgtttca gaagttttg     4806 aattcagtgc atttcctctt gatttgtctg ggttaaaacc attccttttg tatgaaatgt    4866
tttgacttag gaatcatttt atgtacttgt tctacctgga ttgtcaacaa ctgaaagtac    4926
atatttcatc caaatcaagc taaaatttat ttaagttgat tctgagagta caggtcagta    4986
agcctcatta tttggaattt gagagaagta taggtgatcg gatctgtttc atttataaaa    5046
ggtccagttt ttaggactag tacattcctg ttattttctg ggttttatca ttttgcctaa    5106
aataggatat aaaagggaca aaaaataagt agactgtttt tatgtgtgaa ttatatttct    5166
actaaatgtt tttgtatgac tgtgttatac ttgataatat atatatatat atataaaaaa    5226
aaaaaaaaaa aa                                                         5238

<210> SEQ ID NO 2
<211> LENGTH: 1261
<212> TYPE: PRT
<213> ORGANISM: Homo sapiens

<400> SEQUENCE: 2

Met Ile Ala His Lys Gln Lys Thr Lys Lys Arg Ala Trp Ala
  1               5                  10                  15

Ser Gly Gln Leu Ser Thr Asp Ile Thr Thr Ser Glu Met Gly Leu Lys
                 20                  25                  30

Ser Leu Ser Ser Asn Ser Ile Phe Asp Pro Asp Tyr Ile Lys Glu Leu
             35                  40                  45

Val Asn Asp Ile Arg Lys Phe Ser His Ile Leu Leu Tyr Leu Lys Glu
         50                  55                  60

Ala Ile Phe Ser Asp Cys Phe Lys Glu Val Ile His Ile Arg Leu Glu
     65                  70                  75                  80

Glu Leu Leu Arg Val Leu Lys Ser Ile Met Asn Lys His Gln Asn Leu
                 85                  90                  95

Asn Ser Val Asp Leu Gln Asn Ala Ala Glu Met Leu Thr Ala Lys Val
            100                 105                 110

Lys Ala Val Asn Phe Thr Glu Val Asn Glu Glu Asn Lys Asn Asp Leu
        115                 120                 125

Phe Gln Glu Val Phe Ser Ser Ile Glu Thr Leu Ala Phe Thr Phe Gly
    130                 135                 140

Asn Ile Leu Thr Asn Phe Leu Met Gly Asp Val Gly Asn Asp Ser Phe
145                 150                 155                 160

Leu Arg Leu Pro Val Ser Arg Glu Thr Lys Ser Phe Glu Asn Val Ser
                165                 170                 175

Val Glu Ser Val Asp Ser Ser Glu Lys Gly Asn Phe Ser Pro Leu
            180                 185                 190

Glu Leu Asp Asn Val Leu Leu Lys Asn Thr Asp Ser Ile Glu Leu Ala
        195                 200                 205

Leu Ser Tyr Ala Lys Thr Trp Ser Lys Tyr Thr Lys Asn Ile Val Ser
    210                 215                 220

Trp Val Glu Lys Lys Leu Asn Leu Glu Leu Glu Ser Thr Arg Asn Met
225                 230                 235                 240
```

-continued

```
Val Lys Leu Ala Glu Ala Thr Arg Thr Asn Ile Gly Ile Gln Glu Phe
                245                 250                 255

Met Pro Leu Gln Ser Leu Phe Thr Asn Ala Leu Leu Asn Asp Ile Glu
            260                 265                 270

Ser Ser His Leu Leu Gln Gln Thr Ile Ala Ala Leu Gln Ala Asn Lys
        275                 280                 285

Phe Val Gln Pro Leu Leu Gly Arg Lys Asn Glu Met Glu Lys Gln Arg
290                 295                 300

Lys Glu Ile Lys Glu Leu Trp Lys Gln Glu Gln Asn Lys Met Leu Glu
305                 310                 315                 320

Ala Glu Asn Ala Leu Lys Lys Ala Lys Leu Leu Cys Met Gln Arg Gln
                325                 330                 335

Asp Glu Tyr Glu Lys Ala Lys Ser Ser Met Phe Arg Ala Glu Glu Glu
            340                 345                 350

His Leu Ser Ser Ser Gly Gly Leu Ala Lys Asn Leu Asn Lys Gln Leu
        355                 360                 365

Glu Lys Lys Arg Arg Leu Glu Glu Ala Leu Gln Lys Val Glu Glu
370                 375                 380

Ala Asp Glu Leu Tyr Lys Val Cys Val Thr Asn Val Glu Glu Arg Arg
385                 390                 395                 400

Asn Asp Val Glu Asn Thr Lys Arg Glu Ile Leu Ala Gln Leu Arg Thr
                405                 410                 415

Leu Val Phe Gln Cys Asp Leu Thr Leu Lys Ala Val Thr Val Asn Leu
            420                 425                 430

Phe His Met Gln His Leu Gln Ala Ala Ser Leu Ala Asp Arg Leu Gln
        435                 440                 445

Ser Leu Cys Gly Ser Ala Lys Leu Tyr Asp Pro Gly Gln Glu Tyr Ser
    450                 455                 460

Glu Phe Val Lys Ala Thr Asn Ser Thr Glu Glu Lys Val Asp Gly
465                 470                 475                 480

Asn Val Asn Lys His Leu Asn Ser Ser Gln Pro Ser Gly Phe Gly Pro
                485                 490                 495

Ala Asn Ser Leu Glu Asp Val Val Arg Leu Pro Asp Ser Ser Asn Lys
            500                 505                 510

Ile Glu Glu Asp Arg Cys Ser Asn Ser Ala Asp Ile Thr Gly Pro Ser
        515                 520                 525

Phe Ile Arg Ser Trp Thr Phe Gly Met Phe Ser Asp Ser Glu Ser Thr
    530                 535                 540

Gly Gly Ser Ser Glu Ser Arg Ser Leu Asp Ser Glu Ser Ile Ser Pro
545                 550                 555                 560

Gly Asp Phe His Arg Lys Leu Pro Arg Thr Pro Ser Ser Gly Thr Met
                565                 570                 575

Ser Ser Ala Asp Asp Leu Asp Gly Arg Glu Pro Pro Ser Pro Ser Glu
            580                 585                 590

Thr Gly Pro Asn Ser Leu Gly Thr Phe Lys Lys Thr Leu Met Ser Lys
        595                 600                 605

Ala Ala Leu Thr His Lys Phe Arg Lys Leu Arg Ser Pro Thr Lys Cys
    610                 615                 620

Arg Asp Cys Glu Gly Ile Val Val Phe Gln Gly Val Glu Cys Glu Glu
625                 630                 635                 640

Cys Leu Leu Val Cys His Arg Lys Cys Leu Glu Asn Leu Val Ile Ile
                645                 650                 655

Cys Gly His Gln Lys Leu Pro Gly Lys Ile His Leu Phe Gly Ala Glu
```

-continued

```
               660                 665                 670
Phe Thr Leu Val Ala Lys Lys Glu Pro Asp Gly Ile Pro Phe Ile Leu
            675                 680                 685
Lys Ile Cys Ala Ser Glu Ile Glu Asn Arg Ala Leu Cys Leu Gln Gly
690                 695                 700
Ile Tyr Arg Val Cys Gly Asn Lys Ile Lys Thr Glu Lys Leu Cys Leu
705                 710                 715                 720
Ala Leu Glu Asn Gly Met His Leu Val Asp Ile Ser Glu Phe Ser Ser
                725                 730                 735
His Asp Ile Cys Asp Val Leu Lys Leu Tyr Leu Arg Gln Leu Pro Glu
            740                 745                 750
Pro Phe Ile Leu Phe Arg Leu Tyr Lys Glu Phe Ile Asp Leu Ala Lys
            755                 760                 765
Glu Ile Gln His Val Asn Glu Glu Gln Glu Thr Lys Lys Asn Ser Leu
770                 775                 780
Glu Asp Lys Lys Trp Pro Asn Met Cys Ile Glu Ile Asn Arg Ile Leu
785                 790                 795                 800
Leu Lys Ser Lys Asp Leu Leu Arg Gln Leu Pro Ala Ser Asn Phe Asn
                805                 810                 815
Ser Leu His Phe Leu Ile Val His Leu Lys Arg Val Val Asp His Ala
            820                 825                 830
Glu Glu Asn Lys Met Asn Ser Lys Asn Leu Gly Val Ile Phe Gly Pro
            835                 840                 845
Ser Leu Ile Arg Pro Arg Pro Gln Thr Ala Pro Ile Thr Ile Ser Ser
850                 855                 860
Leu Ala Glu Tyr Ser Asn Gln Ala Arg Leu Val Glu Phe Leu Ile Thr
865                 870                 875                 880
Tyr Ser Gln Lys Ile Phe Asp Gly Ser Leu Gln Pro Gln Asp Val Met
                885                 890                 895
Cys Ser Ile Gly Val Val Asp Gln Gly Cys Phe Pro Lys Pro Leu Leu
            900                 905                 910
Ser Pro Glu Glu Arg Asp Ile Glu Arg Ser Met Lys Ser Leu Phe Phe
            915                 920                 925
Ser Ser Lys Glu Asp Ile His Thr Ser Glu Ser Glu Lys Ile Phe
930                 935                 940
Glu Arg Ala Thr Ser Phe Glu Glu Ser Glu Arg Lys Gln Asn Ala Leu
945                 950                 955                 960
Gly Lys Cys Asp Ala Cys Leu Ser Asp Lys Ala Gln Leu Leu Leu Asp
                965                 970                 975
Gln Glu Ala Glu Ser Ala Ser Gln Lys Ile Glu Asp Gly Lys Ala Pro
            980                 985                 990
Lys Pro Leu Ser Leu Lys Ser Asp Arg Ser Thr Asn Asn Val Glu Arg
            995                1000                1005
His Thr Pro Arg Thr Lys Ile Arg Pro Val Ser Leu Pro Val Asp Arg
       1010                1015                1020
Leu Leu Leu Ala Ser Pro Pro Asn Glu Arg Asn Gly Arg Asn Met Gly
1025                1030                1035                1040
Asn Val Asn Leu Asp Lys Phe Cys Lys Asn Pro Ala Phe Glu Gly Val
                1045                1050                1055
Asn Arg Lys Asp Ala Ala Thr Thr Val Cys Ser Lys Phe Asn Gly Phe
            1060                1065                1070
Asp Gln Gln Thr Leu Gln Lys Ile Gln Asp Lys Gln Tyr Glu Gln Asn
       1075                1080                1085
```

```
Ser Leu Thr Ala Lys Thr Thr Met Ile Met Pro Ser Ala Leu Gln Glu
    1090            1095                1100
Lys Gly Val Thr Thr Ser Leu Gln Ile Ser Gly Asp His Ser Ile Asn
1105                1110                1115                1120
Ala Thr Gln Pro Ser Lys Pro Tyr Ala Glu Pro Val Arg Ser Val Arg
                1125                1130                1135
Glu Ala Ser Glu Arg Arg Ser Ser Asp Ser Tyr Pro Leu Ala Pro Val
            1140                1145                1150
Arg Ala Pro Arg Thr Leu Gln Pro Gln His Trp Thr Thr Phe Tyr Lys
        1155                1160                1165
Pro His Ala Pro Ile Ile Ser Ile Arg Gly Asn Glu Glu Lys Pro Ala
    1170                1175                1180
Ser Pro Ser Ala Ala Cys Pro Pro Gly Thr Asp His Asp Pro His Gly
1185                1190                1195                1200
Leu Val Val Lys Ser Met Pro Asp Pro Asp Lys Ala Ser Ala Cys Pro
                1205                1210                1215
Gly Gln Ala Thr Gly Gln Pro Lys Glu Asp Ser Glu Glu Leu Gly Leu
            1220                1225                1230
Pro Asp Val Asn Pro Met Cys Gln Arg Pro Arg Leu Lys Arg Met Gln
        1235                1240                1245
Gln Phe Glu Asp Leu Glu Asp Glu Ile Pro Gln Phe Val
    1250                1255                1260

<210> SEQ ID NO 3
<211> LENGTH: 251
<212> TYPE: DNA
<213> ORGANISM: Homo sapiens
<220> FEATURE:
<221> NAME/KEY: unsure
<222> LOCATION: 201..201
<223> OTHER INFORMATION: n = a, c, g or t

<400> SEQUENCE: 3
ttaatagaaa agacgctgct actactgttt gttccaaatt taatggcttt gaccagcaaa      60
ctctacagaa aattcaggac aaacagtatg aacaaaacag cctaactgcc aagactacaa     120
tgatcatgcc cagtgcactc caggaaaaag gagtgacaac aagcctccag attagtgggg     180
accattctat caatgccact naacccagta agccatatgc agagccagtc aggtcagtga     240
gagaggcatc t                                                         251

<210> SEQ ID NO 4
<211> LENGTH: 256
<212> TYPE: DNA
<213> ORGANISM: Homo sapiens
<220> FEATURE:
<221> NAME/KEY: unsure
<222> LOCATION: 36..36
<223> OTHER INFORMATION: n = a, c, g or t

<400> SEQUENCE: 4
cggtaagcca agctcctcag agtcttcttt aggttnacca gttgcttgcc caggacaagc      60
tgatgctttg tctgggtctg gcattgactt caccacgaga ccgtgggat cgtgatctgt      120 gccaggaggc actgctgctg agggtgaagc tggcttctcc tcattccccc tgatactgat     180
gatgggagca tgtggtttat aaaatgttgt ccaatgttga ggctgcagtg ttctgggtgc     240
tctgacagga gcgaga                                                    256
```

```
<210> SEQ ID NO 5
<211> LENGTH: 298
<212> TYPE: DNA
<213> ORGANISM: Homo sapiens
<220> FEATURE:
<221> NAME/KEY: unsure
<222> LOCATION: 140..140
<223> OTHER INFORMATION: n = a, c, g or t
<220> FEATURE:
<221> NAME/KEY: unsure
<222> LOCATION: 223..223
<223> OTHER INFORMATION: n = a, c, g or t

<400> SEQUENCE: 5
ctttctgtga tagtgccaaa ctctatgacc caggccaaga gtacagtgaa tttgtcaagg      60
ccacaaattc aactgaagaa gaaaaagttg atggaaatgt aaataaacat ttaaatagtt     120
cccaaccttc aggatttggn cctgccaact ctttagagga tgttgtacgc cttcctgaca     180
gttctaataa aattgaagag gacagatgct ctaacagtgc agntataaca ggtccttcct     240
ttataagatc atggacattt gggatgttta gtgattctga gagcactgga gggagcag      298

<210> SEQ ID NO 6
<211> LENGTH: 12
<212> TYPE: DNA
<213> ORGANISM: Homo sapiens

<400> SEQUENCE: 6
ccacaatttg tg                                                          12

<210> SEQ ID NO 7
<211> LENGTH: 4
<212> TYPE: PRT
<213> ORGANISM: Homo sapiens

<400> SEQUENCE: 7

Pro Gln Phe Val
 1

<210> SEQ ID NO 8
<211> LENGTH: 15
<212> TYPE: DNA
<213> ORGANISM: Homo sapiens

<400> SEQUENCE: 8
attccacaat ttgtg                                                       15

<210> SEQ ID NO 9
<211> LENGTH: 5
<212> TYPE: PRT
<213> ORGANISM: Homo sapiens

<400> SEQUENCE: 9

Ile Pro Gln Phe Val
 1               5

<210> SEQ ID NO 10
<211> LENGTH: 18
<212> TYPE: DNA
<213> ORGANISM: Homo sapiens

<400> SEQUENCE: 10
gaaattccac aatttgtg                                                    18

<210> SEQ ID NO 11
```

```
<211> LENGTH: 6
<212> TYPE: PRT
<213> ORGANISM: Homo sapiens

<400> SEQUENCE: 11

Glu Ile Pro Gln Phe Val
1               5

<210> SEQ ID NO 12
<211> LENGTH: 2466
<212> TYPE: PRT
<213> ORGANISM: Homo sapiens

<400> SEQUENCE: 12

Met His Val Ser Leu Ala Glu Ala Leu Glu Val Arg Gly Gly Pro Leu
1               5                   10                  15

Gln Glu Glu Glu Ile Trp Ala Val Leu Asn Gln Ser Ala Glu Ser Leu
            20                  25                  30

Gln Glu Leu Phe Arg Lys Val Ser Leu Ala Asp Pro Ala Ala Leu Gly
        35                  40                  45

Phe Ile Ile Ser Pro Trp Ser Leu Leu Leu Pro Ser Gly Ser Val
    50                  55                  60

Ser Phe Thr Asp Glu Asn Ile Ser Asn Gln Asp Leu Arg Ala Phe Thr
65                  70                  75                  80

Ala Pro Glu Val Leu Gln Asn Gln Ser Leu Thr Ser Leu Ser Asp Val
                85                  90                  95

Glu Lys Ile His Ile Tyr Ser Leu Gly Met Thr Leu Tyr Trp Gly Ala
                100                 105                 110

Asp Tyr Glu Val Pro Gln Ser Gln Pro Ile Lys Leu Gly Asp His Leu
            115                 120                 125

Asn Ser Ile Leu Leu Gly Met Cys Glu Asp Val Ile Tyr Ala Arg Val
130                 135                 140

Ser Val Arg Thr Val Leu Asp Ala Cys Ser Ala His Ile Arg Asn Ser
145                 150                 155                 160

Asn Cys Ala Pro Ser Phe Ser Tyr Val Lys His Leu Val Lys Leu Val
                165                 170                 175

Leu Gly Asn Leu Ser Gly Thr Asp Gln Leu Ser Cys Asn Ser Glu Gln
            180                 185                 190

Lys Pro Asp Arg Ser Gln Ala Ile Arg Asp Arg Leu Arg Gly Lys Gly
        195                 200                 205

Leu Pro Thr Gly Arg Ser Ser Thr Ser Asp Val Leu Asp Ile Gln Lys
    210                 215                 220

Pro Pro Leu Ser His Gln Thr Phe Leu Asn Lys Gly Leu Ser Lys Ser
225                 230                 235                 240

Met Gly Phe Leu Ser Ile Lys Asp Thr Gln Asp Glu Asn Tyr Phe Lys
                245                 250                 255

Asp Ile Leu Ser Asp Asn Ser Gly Arg Glu Asp Ser Glu Asn Thr Phe
            260                 265                 270

Ser Pro Tyr Gln Phe Lys Thr Ser Gly Pro Glu Lys Lys Pro Ile Pro
        275                 280                 285

Gly Ile Asp Val Leu Ser Lys Lys Ile Trp Ala Ser Ser Met Asp
    290                 295                 300

Leu Leu Cys Thr Ala Asp Arg Asp Phe Ser Ser Gly Glu Thr Ala Thr
305                 310                 315                 320

Tyr Arg Arg Cys His Pro Glu Ala Val Thr Val Arg Thr Ser Thr Thr
                325                 330                 335
```

-continued

```
Pro Arg Lys Lys Glu Ala Arg Tyr Ser Asp Gly Ser Ile Ala Leu Asp
        340                 345                 350

Ile Phe Gly Pro Gln Lys Met Asp Pro Ile Tyr His Thr Arg Glu Leu
        355                 360                 365

Pro Thr Ser Ser Ala Ile Ser Ser Ala Leu Asp Arg Ile Arg Glu Arg
        370                 375                 380

Gln Lys Lys Leu Gln Val Leu Arg Glu Ala Met Asn Val Glu Glu Pro
385                 390                 395                 400

Val Arg Arg Tyr Lys Thr Tyr His Gly Asp Val Phe Ser Thr Ser Ser
                405                 410                 415

Glu Ser Pro Ser Ile Ile Ser Ser Glu Ser Asp Phe Arg Gln Val Arg
                420                 425                 430

Arg Ser Glu Ala Ser Lys Arg Phe Glu Ser Ser Ser Gly Leu Pro Gly
        435                 440                 445

Val Asp Glu Thr Leu Ser Gln Gly Gln Ser Gln Arg Pro Ser Arg Gln
        450                 455                 460

Tyr Glu Thr Pro Phe Glu Gly Asn Leu Ile Asn Gln Glu Ile Met Leu
465                 470                 475                 480

Lys Arg Gln Glu Glu Glu Leu Met Gln Leu Gln Ala Lys Met Ala Leu
                485                 490                 495

Arg Gln Ser Arg Leu Ser Leu Tyr Pro Gly Asp Thr Ile Lys Ala Ser
        500                 505                 510

Met Leu Asp Ile Thr Arg Asp Pro Leu Arg Glu Ile Ala Leu Glu Thr
        515                 520                 525

Ala Met Thr Gln Arg Lys Leu Arg Asn Phe Phe Gly Pro Glu Phe Val
        530                 535                 540

Lys Met Thr Ile Glu Pro Phe Ile Ser Leu Asp Leu Pro Arg Ser Ile
545                 550                 555                 560

Leu Thr Lys Lys Gly Lys Asn Glu Asp Asn Arg Arg Lys Val Asn Ile
                565                 570                 575

Met Leu Leu Asn Gly Gln Arg Leu Glu Leu Thr Cys Asp Thr Lys Thr
        580                 585                 590

Ile Cys Lys Asp Val Phe Asp Met Val Val Ala His Ile Gly Leu Val
        595                 600                 605

Glu His His Leu Phe Ala Leu Ala Thr Leu Lys Asp Asn Glu Tyr Phe
        610                 615                 620

Phe Val Asp Pro Asp Leu Lys Leu Thr Lys Val Ala Pro Glu Gly Trp
625                 630                 635                 640

Lys Glu Glu Pro Lys Lys Thr Lys Ala Thr Val Asn Phe Thr Leu
                645                 650                 655

Phe Phe Arg Ile Lys Phe Phe Met Asp Asp Val Ser Leu Ile Gln His
                660                 665                 670

Thr Leu Thr Cys His Gln Tyr Leu Gln Leu Arg Lys Asp Ile Leu
        675                 680                 685

Glu Glu Arg Met His Cys Asp Asp Glu Thr Ser Leu Leu Leu Ala Ser
        690                 695                 700

Leu Ala Leu Gln Ala Glu Tyr Gly Asp Tyr Gln Pro Glu Val His Gly
705                 710                 715                 720

Val Ser Tyr Phe Arg Met Glu His Tyr Leu Pro Ala Arg Val Met Glu
                725                 730                 735

Lys Leu Asp Leu Ser Tyr Ile Lys Glu Glu Leu Pro Lys Leu His Asn
                740                 745                 750
```

-continued

```
Thr Tyr Val Gly Ala Ser Glu Lys Glu Thr Glu Leu Glu Phe Leu Lys
            755                 760                 765
Val Cys Gln Arg Leu Thr Glu Tyr Gly Val His Phe His Arg Val His
        770                 775                 780
Pro Glu Lys Lys Ser Gln Thr Gly Ile Leu Leu Gly Val Cys Ser Lys
785                 790                 795                 800
Gly Val Leu Val Phe Glu Val His Asn Gly Val Arg Thr Leu Val Leu
                805                 810                 815
Arg Phe Pro Trp Arg Glu Thr Lys Lys Ile Ser Phe Ser Lys Lys Lys
            820                 825                 830
Ile Thr Leu Gln Asn Thr Ser Asp Gly Ile Lys His Gly Phe Gln Thr
        835                 840                 845
Asp Asn Ser Lys Ile Cys Gln Tyr Leu Leu His Leu Cys Ser Tyr Gln
850                 855                 860
His Lys Phe Gln Leu Gln Met Arg Ala Arg Gln Ser Asn Gln Asp Ala
865                 870                 875                 880
Gln Asp Ile Glu Arg Ala Ser Phe Arg Ser Leu Asn Leu Gln Ala Glu
            885                 890                 895
Ser Val Arg Gly Phe Asn Met Gly Arg Ala Ile Ser Thr Gly Ser Leu
        900                 905                 910
Ala Ser Ser Thr Leu Asn Lys Leu Ala Val Arg Pro Leu Ser Val Gln
        915                 920                 925
Ala Glu Ile Leu Lys Arg Leu Ser Cys Ser Glu Leu Ser Leu Tyr Gln
        930                 935                 940
Pro Leu Gln Asn Ser Ser Lys Glu Lys Asn Asp Lys Ala Ser Trp Glu
945                 950                 955                 960
Glu Lys Pro Arg Glu Met Ser Lys Ser Tyr His Asp Leu Ser Gln Ala
            965                 970                 975
Ser Leu Tyr Pro His Arg Lys Asn Val Ile Val Asn Met Glu Pro Pro
            980                 985                 990
Pro Gln Thr Val Ala Glu Leu Val Gly Lys Pro Ser His Gln Met Ser
        995                 1000                1005
Arg Ser Asp Ala Glu Ser Leu Ala Gly Val Thr Lys Leu Asn Asn Ser
        1010                1015                1020
Lys Ser Val Ala Ser Leu Asn Arg Ser Pro Glu Arg Arg Lys His Glu
1025                1030                1035                1040
Ser Asp Ser Ser Ser Ile Glu Asp Pro Gly Gln Ala Tyr Val Leu Asp
                1045                1050                1055
Val Leu His Lys Arg Trp Ser Ile Val Ser Ser Pro Glu Arg Glu Ile
                1060                1065                1070
Thr Leu Val Asn Leu Lys Lys Asp Ala Lys Tyr Gly Leu Gly Phe Gln
        1075                1080                1085
Ile Ile Gly Gly Glu Lys Met Gly Arg Leu Asp Leu Gly Ile Phe Ile
        1090                1095                1100
Ser Ser Val Ala Pro Gly Gly Pro Ala Asp Phe His Gly Cys Leu Lys
1105                1110                1115                1120
Pro Gly Asp Arg Leu Ile Ser Val Asn Ser Val Ser Leu Glu Gly Val
            1125                1130                1135
Ser His His Ala Ala Ile Glu Ile Leu Gln Asn Ala Pro Glu Asp Val
            1140                1145                1150
Thr Leu Val Ile Ser Gln Pro Lys Glu Lys Ile Ser Lys Val Pro Ser
        1155                1160                1165
Thr Pro Val His Leu Thr Asn Glu Met Lys Asn Tyr Met Lys Lys Ser
```

-continued

```
          1170                1175                1180
Ser Tyr Met Gln Asp Ser Ala Ile Asp Ser Ser Lys Asp His His
1185                1190                1195                1200

Trp Ser Arg Gly Thr Leu Arg His Ile Ser Glu Asn Ser Phe Gly Pro
               1205                1210                1215

Ser Gly Gly Leu Arg Glu Gly Ser Leu Ser Ser Gln Asp Ser Arg Thr
               1220                1225                1230

Glu Ser Ala Ser Leu Ser Gln Ser Gln Val Asn Gly Phe Phe Ala Ser
               1235                1240                1245

His Leu Gly Asp Gln Thr Trp Gln Glu Ser Gln His Gly Ser Pro Ser
               1250                1255                1260

Pro Ser Val Ile Ser Lys Ala Thr Glu Lys Glu Thr Phe Thr Asp Ser
1265                1270                1275                1280

Asn Gln Ser Lys Thr Lys Lys Pro Gly Ile Ser Asp Val Thr Asp Tyr
               1285                1290                1295

Ser Asp Arg Gly Asp Ser Asp Met Asp Glu Ala Thr Tyr Ser Ser Ser
               1300                1305                1310

Gln Asp His Gln Thr Pro Lys Gln Glu Ser Ser Ser Val Asn Thr
               1315                1320                1325

Ser Asn Lys Met Asn Phe Lys Thr Phe Ser Ser Pro Pro Lys Pro
               1330                1335                1340

Gly Asp Ile Phe Glu Val Glu Leu Ala Lys Asn Asp Asn Ser Leu Gly
1345                1350                1355                1360

Ile Ser Val Thr Gly Gly Val Asn Thr Ser Val Arg His Gly Gly Ile
               1365                1370                1375

Tyr Val Lys Ala Val Ile Pro Gln Gly Ala Ala Glu Ser Asp Gly Arg
               1380                1385                1390

Ile His Lys Gly Asp Arg Val Leu Ala Val Asn Gly Val Ser Leu Glu
               1395                1400                1405

Gly Ala Thr His Lys Gln Ala Val Glu Thr Leu Arg Asn Thr Gly Gln
               1410                1415                1420

Val Val His Leu Leu Leu Glu Lys Gly Gln Ser Pro Thr Ser Lys Glu
1425                1430                1435                1440

His Val Pro Val Thr Pro Gln Cys Thr Leu Ser Asp Gln Asn Ala Gln
               1445                1450                1455

Gly Gln Gly Pro Glu Lys Val Lys Thr Thr Gln Val Lys Asp Tyr
               1460                1465                1470

Ser Phe Val Thr Glu Glu Asn Thr Phe Glu Val Lys Leu Phe Lys Asn
               1475                1480                1485

Ser Ser Gly Leu Gly Phe Ser Phe Ser Arg Glu Asp Asn Leu Ile Pro
               1490                1495                1500

Glu Gln Ile Asn Ala Ser Ile Val Arg Val Lys Lys Leu Phe Ala Gly
1505                1510                1515                1520

Gln Pro Ala Ala Glu Ser Gly Lys Ile Asp Val Gly Asp Val Ile Leu
               1525                1530                1535

Lys Val Asn Gly Ala Ser Leu Lys Gly Leu Ser Gln Gln Glu Val Ile
               1540                1545                1550

Ser Ala Leu Arg Gly Thr Ala Pro Glu Val Phe Leu Leu Leu Cys Arg
               1555                1560                1565

Pro Pro Pro Gly Val Leu Pro Glu Ile Asp Thr Ala Leu Leu Thr Pro
               1570                1575                1580

Leu Gln Ser Pro Ala Gln Val Leu Pro Asn Ser Ser Lys Asp Ser Ser
1585                1590                1595                1600
```

```
Gln Pro Ser Cys Val Glu Gln Ser Thr Ser Ser Asp Glu Asn Glu Met
            1605                1610                1615

Ser Asp Lys Ser Lys Lys Gln Cys Lys Ser Pro Ser Arg Arg Asp Ser
            1620                1625                1630

Tyr Ser Asp Ser Ser Gly Ser Gly Glu Asp Asp Leu Val Thr Ala Pro
            1635                1640                1645

Ala Asn Ile Ser Asn Ser Thr Trp Ser Ser Ala Leu His Gln Thr Leu
            1650                1655                1660

Ser Asn Met Val Ser Gln Ala Gln Ser His His Glu Ala Pro Lys Ser
1665                1670                1675                1680

Gln Glu Asp Thr Ile Cys Thr Met Phe Tyr Tyr Pro Gln Lys Ile Pro
            1685                1690                1695

Asn Lys Pro Glu Phe Glu Asp Ser Asn Pro Ser Pro Leu Pro Pro Asp
            1700                1705                1710

Met Ala Pro Gly Gln Ser Tyr Gln Pro Gln Ser Glu Ser Ala Ser Ser
            1715                1720                1725

Ser Ser Met Asp Lys Tyr His Ile His His Ile Ser Glu Pro Thr Arg
            1730                1735                1740

Gln Glu Asn Trp Thr Pro Leu Lys Asn Asp Leu Glu Asn His Leu Glu
1745                1750                1755                1760

Asp Phe Glu Leu Glu Val Glu Leu Leu Ile Thr Leu Ile Lys Ser Glu
            1765                1770                1775

Lys Ala Ser Leu Gly Phe Thr Val Thr Lys Gly Asn Gln Arg Ile Gly
            1780                1785                1790

Cys Tyr Val His Asp Val Ile Gln Asp Pro Ala Lys Ser Asp Gly Arg
            1795                1800                1805

Leu Lys Pro Gly Asp Arg Leu Ile Lys Val Asn Asp Thr Asp Val Thr
            1810                1815                1820

Asn Met Thr His Thr Asp Ala Val Asn Leu Leu Arg Ala Ala Ser Lys
1825                1830                1835                1840

Thr Val Arg Leu Val Ile Gly Arg Val Leu Glu Leu Pro Arg Ile Pro
            1845                1850                1855

Met Leu Pro His Leu Leu Pro Asp Ile Thr Leu Thr Cys Asn Lys Glu
            1860                1865                1870

Glu Leu Gly Phe Ser Leu Cys Gly Gly His Asp Ser Leu Tyr Gln Val
            1875                1880                1885

Val Tyr Ile Ser Asp Ile Asn Pro Arg Ser Val Ala Ala Ile Glu Gly
            1890                1895                1900

Asn Leu Gln Leu Leu Asp Val Ile His Tyr Val Asn Gly Val Ser Thr
1905                1910                1915                1920

Gln Gly Met Thr Leu Glu Glu Val Asn Arg Ala Leu Asp Met Ser Leu
            1925                1930                1935

Pro Ser Leu Val Leu Lys Ala Thr Arg Asn Asp Leu Pro Val Val Pro
            1940                1945                1950

Ser Ser Lys Arg Ser Ala Val Ser Ala Pro Lys Ser Thr Lys Gly Asn
            1955                1960                1965

Gly Ser Tyr Ser Val Gly Ser Cys Ser Gln Pro Ala Leu Thr Pro Asn
            1970                1975                1980

Asp Ser Phe Ser Thr Val Ala Gly Glu Glu Ile Asn Glu Ile Ser Tyr
1985                1990                1995                2000

Pro Lys Gly Lys Cys Ser Thr Tyr Gln Ile Lys Gly Ser Pro Asn Leu
            2005                2010                2015
```

```
Thr Leu Pro Lys Glu Ser Tyr Ile Gln Glu Asp Asp Ile Tyr Asp Asp
            2020                2025                2030

Ser Gln Glu Ala Glu Val Ile Gln Ser Leu Leu Asp Val Val Asp Glu
        2035                2040                2045

Glu Ala Gln Asn Leu Leu Asn Glu Asn Asn Ala Ala Gly Tyr Ser Cys
        2050                2055                2060

Gly Pro Gly Thr Leu Lys Met Asn Gly Lys Leu Ser Glu Glu Arg Thr
2065                2070                2075                2080

Glu Asp Thr Asp Cys Asp Gly Ser Pro Leu Pro Glu Tyr Phe Thr Glu
            2085                2090                2095

Ala Thr Lys Met Asn Gly Cys Glu Glu Tyr Cys Glu Glu Lys Val Lys
        2100                2105                2110

Ser Glu Ser Leu Ile Gln Lys Pro Gln Glu Lys Lys Thr Asp Asp Asp
        2115                2120                2125

Glu Ile Thr Trp Gly Asn Asp Glu Leu Pro Ile Glu Arg Thr Asn His
        2130                2135                2140

Glu Asp Ser Asp Lys Asp His Ser Phe Leu Thr Asn Asp Glu Leu Ala
2145                2150                2155                2160

Val Leu Pro Val Val Lys Val Leu Pro Ser Gly Lys Tyr Thr Gly Ala
            2165                2170                2175

Asn Leu Lys Ser Val Ile Arg Val Leu Arg Gly Leu Leu Asp Gln Gly
        2180                2185                2190

Ile Pro Ser Lys Glu Leu Glu Asn Leu Gln Glu Leu Lys Pro Leu Asp
        2195                2200                2205

Gln Cys Leu Ile Gly Gln Thr Lys Glu Asn Arg Arg Lys Asn Arg Tyr
        2210                2215                2220

Lys Asn Ile Leu Pro Tyr Asp Ala Thr Arg Val Pro Leu Gly Asp Glu
2225                2230                2235                2240

Gly Gly Tyr Ile Asn Ala Ser Phe Ile Lys Ile Pro Val Gly Lys Glu
            2245                2250                2255

Glu Phe Val Tyr Ile Ala Cys Gln Gly Pro Leu Pro Thr Thr Val Gly
            2260                2265                2270

Asp Phe Trp Gln Met Ile Trp Glu Gln Lys Ser Thr Val Ile Ala Met
        2275                2280                2285

Met Thr Gln Glu Val Glu Gly Glu Lys Ile Lys Cys Gln Arg Tyr Trp
        2290                2295                2300

Pro Asn Ile Leu Gly Lys Thr Thr Met Val Ser Asn Arg Leu Arg Leu
2305                2310                2315                2320

Ala Leu Val Arg Met Gln Gln Leu Lys Gly Phe Val Val Arg Ala Met
            2325                2330                2335

Thr Leu Glu Asp Ile Gln Thr Arg Glu Val Arg His Ile Ser His Leu
            2340                2345                2350

Asn Phe Thr Ala Trp Pro Asp His Asp Thr Pro Ser Gln Pro Asp Asp
        2355                2360                2365

Leu Leu Thr Phe Ile Ser Tyr Met Arg His Ile His Arg Ser Gly Pro
        2370                2375                2380

Ile Ile Thr His Cys Ser Ala Gly Ile Gly Arg Ser Gly Thr Leu Ile
2385                2390                2395                2400

Cys Ile Asp Val Val Leu Gly Leu Ile Ser Gln Asp Leu Asp Phe Asp
            2405                2410                2415

Ile Ser Asp Leu Val Arg Cys Met Arg Leu Gln Arg His Gly Met Val
            2420                2425                2430

Gln Thr Glu Asp Gln Tyr Ile Phe Cys Tyr Gln Val Ile Leu Tyr Val
```

-continued

```
             2435                2440                2445
Leu Thr Arg Leu Gln Ala Glu Glu Gln Lys Gln Gln Pro Gln Leu
        2450                2455                2460
Leu Lys
2465
```

<210> SEQ ID NO 13
<211> LENGTH: 322
<212> TYPE: PRT
<213> ORGANISM: Homo sapiens

<400> SEQUENCE: 13

```
Glu Ile Asp Lys Leu Leu Ile Ser Arg Thr Asp Gly Val Asp Val Ala
 1               5                  10                  15

Phe Glu Arg Thr Lys Ala Trp Ser Thr Tyr Ser Lys Asp Val Ile Ser
            20                  25                  30

Tyr Val Arg Ala Arg Ile Gln Leu Glu Gln Asp His Ala Arg Lys Val
        35                  40                  45

His Thr Leu Val Asp Thr Ser Arg Arg Asp Ile Asn Lys Pro Phe Met
    50                  55                  60

Pro Leu Arg Glu Ile Phe Glu Asn Ser Phe Asp Thr Glu Val Glu Met
65                  70                  75                  80

Val Thr His Thr Lys Glu Thr Glu His Leu Lys Asp Arg Val Val
                85                  90                  95

Glu Ala Leu Asp Ala Arg Arg Lys Glu His Asp Thr Val Arg Asn Ala
            100                 105                 110

Leu Lys Val Glu Trp Thr Lys Ala Thr Lys Ser Leu His Asp Cys Glu
        115                 120                 125

Glu Ser Tyr Glu Lys Ser Lys Ile Thr Leu Arg Met Arg Glu Glu Ala
    130                 135                 140

Leu Lys Lys Ala Arg Glu Ser Cys Leu Arg Thr Glu Ser Ser Pro Pro
145                 150                 155                 160

Glu Arg Glu Ala Ser Arg Arg Arg Asp Leu Glu Lys Lys Ser Arg
                165                 170                 175

Ala Val Glu Glu Ala Met Ile Lys Lys Glu Glu Ala Glu Arg Gln Val
            180                 185                 190

Val Ser Ile Thr Ala Glu Leu Arg Lys Lys Arg Arg Asp Ile Asp Lys
        195                 200                 205

Thr Lys Glu Ser Val Val Glu Arg Leu Arg Glu Leu Ile Phe Gln Cys
    210                 215                 220

Glu Gln Thr Thr Lys Ala Cys Thr Val His Tyr Phe Thr Ser Leu Ala
225                 230                 235                 240

Ala Leu Trp Ala Arg Leu Pro Gly Ala Phe His Glu Leu Ser Asn Ala
                245                 250                 255

Thr Arg Asp Tyr Gln Pro Gly Thr Glu Tyr Met Ala Phe Leu Gln Thr
            260                 265                 270

Leu Pro Thr Arg Ala Ala Ser Ser Ser Leu Val Arg Ser Asp Arg
        275                 280                 285

Ser Ile Asp Glu Gly Val Ala Ser Cys Asp Gly Ser Ser Ser Leu Thr
    290                 295                 300

Ser Leu Arg Arg Asn Ala Ile Asn Pro Asp Asp Glu Gly Ala Leu Pro
305                 310                 315                 320

Asp Thr
```

<210> SEQ ID NO 14
<211> LENGTH: 451
<212> TYPE: DNA
<213> ORGANISM: Homo sapiens

<400> SEQUENCE: 14

```
caaaaaagaa tagtcttgaa gacaaaaaat ggccaaatat gtgtatagaa ataaaccgaa      60
ttcttctaaa aagcaaagac cttctaagac aattgccagc atcaaatttt aacagtcttc     120
atttccttat agtacatcta aagcgggtag tagatcatgc agaagaaaac aagatgaact     180
ccaaaaactt gggggtgata tttggaccaa gtctcattag gccaaggcca caactgctcc     240
tatcaccatc tcctcccttg cagagtattc aaatcaagca cgcttggtag agtttctcat     300
tacttactca cagaagatct tcgatgggtc cctacagcca agatgttta tgtgtagcat     360 aggtgttgtt gatcaaggct gttttccaaa gcctctgtta tcaccagaag aaagagacat     420
tgaacgttcc atgaagtcac tatttttttc t                                    451
```

<210> SEQ ID NO 15
<211> LENGTH: 543
<212> TYPE: DNA
<213> ORGANISM: Homo sapiens

<400> SEQUENCE: 15

```
gtcaagatga atatgagaaa gcaaagtctt ccatgtttcg tgcagaagag gagcatctgt      60
cttcaagtgg cggattagca aaaatctca acaagcaact agaaaaaaag cgaaggttgg      120
aagaggaggc tctccaaaaa gtagaagaag caaatgaact ttacaaagtt tgtgtgacaa     180
atgttgaaga agaagaaat gatctagaaa ataccaaaag agaaatttta gcacaactcc     240
ggacacttgt tttccagtgt gatcttaccc ttaaagctgt aacagttaac ctcttccaca     300
tgcagcatct gcaggctgct tcccttgcag acagtttaca gtctctctgt gatagtgcca     360
aactcttatg acccaggcca agagtacagt ggaattttgt tcaaggccac aaatttcaac     420
tgaaggaagg aaaaagttga tgggaatgta aataaacatt ttaaatagtt cccaaccttc     480
agggtttggg cctgccaatt tttaggggt gttgtacggc ttcctgacag ttcttataaa     540
att                                                                   543
```

<210> SEQ ID NO 16
<211> LENGTH: 347
<212> TYPE: DNA
<213> ORGANISM: Homo sapiens
<220> FEATURE:
<221> NAME/KEY: unsure
<222> LOCATION: 321..321
<223> OTHER INFORMATION: n = a, c, g or t

<400> SEQUENCE: 16

```
agaccaagag gctgaatcag catcccaaaa gatagaagat ggtaaaaccc ctaagccact      60
ttctctgaaa tctgataggt caacaaacaa tgtggagagg catactccaa ggaccaagat     120
tagacctgta agtttgcctg tagatagact acttcttgca agtcctccta atgagagaaa     180
tggcagaaat atgggaaatg taaatttaga caagttttgc aagaatcctg cctttgaagg     240
agttaataga aaagacgctg ctactactgt tgttccaaa tttaatggct ttgaccagca     300
aactctacag aaaattcagg ncaaacagta tgaacaaaac agcttaa                   347
```

<210> SEQ ID NO 17
<211> LENGTH: 458
<212> TYPE: DNA

```
<213> ORGANISM: Mus musculus

<400> SEQUENCE: 17
cttatgggag acgtaggcag tgactcgata ctacgtctac ctatttctcg agaaagtaag      60
tcttttgaaa acatttctgt ggactcagtg gacttacccc atgaaaaagg aaattttct     120 cctatagaac tagacaactt gctgttaaag aacactgact ctatagagct ggctttgtcc    180
tatgctaaaa catggtcaaa ataccaag aatatagtgt cgtgggttga aaaaagctc       240 aacttggaat tggagtccac tagaaatatt gtaaaattgg cagaggcaac tagatctagc    300
attggtatac aagagtttat gccactgcag tctctattta ccaacgctct tctcagtgac    360
atccacagca gccaccttct acaacagaca attgcagccc tccaagccaa taaatttgtg    420
cagcctctac ttgggaggaa gaatgagatg gagaaaaaa                            458

<210> SEQ ID NO 18
<211> LENGTH: 308
<212> TYPE: DNA
<213> ORGANISM: Homo sapiens
<220> FEATURE:
<221> NAME/KEY: unsure
<222> LOCATION: 20..20
<223> OTHER INFORMATION: n = a, c, g or t
<220> FEATURE:
<221> NAME/KEY: unsure
<222> LOCATION: 30..30
<223> OTHER INFORMATION: n = a, c, g or t
<220> FEATURE:
<221> NAME/KEY: unsure
<222> LOCATION: 31..31
<223> OTHER INFORMATION: n = a, c, g or t
<220> FEATURE:
<221> NAME/KEY: unsure
<222> LOCATION: 280..280
<223> OTHER INFORMATION: n = a, c, g or t

<400> SEQUENCE: 18
caaaacagcc taactgccan gactacaatn ntcatgccca gtgcactcca ggaaaaagga     60
gtgacaacaa gcctccagat tagtggggac cattctatca atgccactca acccagtaag   120
ccatatgcag agccagtcag gtcagtgaga gaggcatctg agagacggtc ttcagattcc   180
taccctctcg ctcctgtcag agcacccaga acactgcagc ctcaacattg gacaacattt   240
tataaaccac atgctcccat catcagtatc aggggaatn aggagaagcc agtttcaccc    300
tcagcagc                                                             308

<210> SEQ ID NO 19
<211> LENGTH: 443
<212> TYPE: DNA
<213> ORGANISM: Homo sapiens
<220> FEATURE:
<221> NAME/KEY: unsure
<222> LOCATION: 59..59
<223> OTHER INFORMATION: n = a, c, g or t

<400> SEQUENCE: 19
tgccactcaa cccagtaagc catatgcaga gccagtcagg tcagtgagag aggcatctna     60
gagacggtct tcagattcct accctctcgc tcctgtcaga gcacccagaa cactgcagcc   120
tcaacattgg acaacatttt ataaaccaca tgctcccatc atcagtatca ggggaatga    180 ggagaagcca gcttcaccct cagcagcagt gcctcctggc acagatcacg atccccacgg   240
tctcgtggtg aagtcaatgc cagacccaga caaagcatca gcttgtcctg ggcaagcaa    300 ctggtcaacc taaagaagac ttttgaggga gcttgggttt gcctgatgtg aatccaatg    360
```

```
tgttcagagg accaaggctt aaaacggatt gcaaacagtt ttgaaggacc tcggaggtgg      420
aatttccaca atttttttta ggg                                              443
```

<210> SEQ ID NO 20
<211> LENGTH: 302
<212> TYPE: DNA
<213> ORGANISM: Homo sapiens
<220> FEATURE:
<221> NAME/KEY: unsure
<222> LOCATION: 260..260
<223> OTHER INFORMATION: n = a, c, g or t

<400> SEQUENCE: 20

```
ctactgtttg ttccaaattt aatggctttg accagcaaac tctacagaaa attcaggaca       60
aacagtatga acaaaacagc ctaactgcca agactacaat gatcatgccc agtgcactcc      120
aggaaaaagg agtgacaaca agcctccaga ttagtgggga ccattctatc aatgccactc      180
aacccagtaa gccatatgca gagccagtca ggtcagtgag agaggcatct gagagacggt      240
cttcagattc ctaccctctn gctcctgtca gagcacccag aacactgcag ccttcaacat      300
tg                                                                     302
```

<210> SEQ ID NO 21
<211> LENGTH: 287
<212> TYPE: DNA
<213> ORGANISM: Homo sapiens

<400> SEQUENCE: 21

```
aagctttgga aaatggaatg cacttggtag atatttcaga atttagttca catgatatct       60
gtgacgtctt gaaattatac cttcggcagc tcccagaacc atttatttta tttcgattgt      120
acaaggaatt tatagacctt gcaaaagaga tccaacatgt aaatgaagaa caagagacaa      180 aaagaatag tcttgaagac aaaaaatggc caaatatgtg tatagaaata aaccgaattc       240
ttctaaaaag caaagacctt ctaagacaat tgccagcatc aaatttt                    287
```

<210> SEQ ID NO 22
<211> LENGTH: 332
<212> TYPE: DNA
<213> ORGANISM: Homo sapiens
<220> FEATURE:
<221> NAME/KEY: unsure
<222> LOCATION: 261..261
<223> OTHER INFORMATION: n = a, c, g or t
<220> FEATURE:
<221> NAME/KEY: unsure
<222> LOCATION: 299..299
<223> OTHER INFORMATION: n = a, c, g or t
<220> FEATURE:
<221> NAME/KEY: unsure
<222> LOCATION: 320..320
<223> OTHER INFORMATION: n = a, c, g or t
<220> FEATURE:
<221> NAME/KEY: unsure
<222> LOCATION: 326..326
<223> OTHER INFORMATION: n = a, c, g or t

<400> SEQUENCE: 22

```
cggaccaagt tcattaggc caaggcccac aactgctcct atcaccatct cctcccttgc        60
agagtattca aatcaagcac gcttggtaga gtttctcatt acttactcac agaagatctt      120
cgatgggtcc ctacaaccac aagatgttat gtgtagcata ggtgttgttg atcaaggctg      180
ttttccaaag cctctgttat caccagaaga aagagacatt gaacgttcca tgaagtcact      240
```

```
attttttttct tcaaaggaag ntatccatac ttcagagagt gaaagcaaaa tttttgaanc      300
gggctacatc attttgaggn atcagnacgc at                                    332
```

<210> SEQ ID NO 23
<211> LENGTH: 545
<212> TYPE: DNA
<213> ORGANISM: Mus musculus
<220> FEATURE:
<221> NAME/KEY: unsure
<222> LOCATION: 509..509
<223> OTHER INFORMATION: n = a, c, g or t

<400> SEQUENCE: 23

```
tgaccaagag catgagtcag cgtcccaaaa gatggaagat gtctgtaaaa gccccaagct      60
gctgctgctg aaatccaata gggcagcaaa cagtgtgcag agacatactc caaggaccaa     120
gatgagacct gtaagcttgc ctgtagaccg gctgcttctt cttgccagtt ctcctactga     180
gagaagcagc agggatgtag gaaacgtaga ctcagacaag tttggcaaga accctgcctt     240
tgaaggactc catagaaagg acaactcaaa tactactcgc tccaaagtta atggctttga     300
ccagcaaaat gtacagaaat cctgggacac acaatatgta cggaacaatt ttactgccaa     360
gactacgatg attgttccca gtgcctaccc tgagaaggga ttgacagtaa acactgggaa     420
taacagggac catcccggca gtaaagcaca tgcagagcca gccagggctg caggagatgt     480
gtcagagcgc aggtcctctg actcctgcnc cgccactgct gtcagagcac ccagaacact     540
gcagc                                                                 545
```

<210> SEQ ID NO 24
<211> LENGTH: 261
<212> TYPE: DNA
<213> ORGANISM: Homo sapiens
<220> FEATURE:
<221> NAME/KEY: unsure
<222> LOCATION: 218..218
<223> OTHER INFORMATION: n = a, c, g or t

<400> SEQUENCE: 24

```
ctactgtttg ttccaaattt aatggctttg accagcaaac tctacagaaa attcaggaca      60
aacagtatga acaaaacagc ctaactgcca agactacaat gatcatgccc agtgcactcc     120
aggaaaaagg agtgacaaca agcctccaga ttagtgggga ccattctatc aatgccactc     180
aacccagtaa gccatatgca gagccagtca ggtcagtnag agaggcatct gagagacggt     240
cttcagattc ctaccctctc g                                               261
```

<210> SEQ ID NO 25
<211> LENGTH: 321
<212> TYPE: DNA
<213> ORGANISM: Homo sapiens
<220> FEATURE:
<221> NAME/KEY: unsure
<222> LOCATION: 11..11
<223> OTHER INFORMATION: n = a, c, g or t
<220> FEATURE:
<221> NAME/KEY: unsure
<222> LOCATION: 284..284
<223> OTHER INFORMATION: n = a, c, g or t

<400> SEQUENCE: 25

```
ctcgtgcgcc ncttgcagag tattcaaatc aagcacgctt ggtagagttt ctcattactt      60
actcacagaa gatcttcgat gggtccctac aaccacaaga tgttatgtgt agcataggtg     120
ttgttgatca aggctgtttt ccaaagcctc tgttatcacc agaagaaaga gacattgaac     180
```

```
gttccatgaa gtcactattt ttttcttcaa aggaagatat ccatacttca gagagtgaaa      240
gcaaaatttt tgaacgagct acatcatttt gagggaatca gaancgcaag caaaatgcgt      300
tagggaaaat gtggatgcaa t                                                 321

<210> SEQ ID NO 26
<211> LENGTH: 298
<212> TYPE: DNA
<213> ORGANISM: Homo sapiens
<220> FEATURE:
<221> NAME/KEY: unsure
<222> LOCATION: 254..254
<223> OTHER INFORMATION: n = a, c, g or t
<220> FEATURE:
<221> NAME/KEY: unsure
<222> LOCATION: 274..274
<223> OTHER INFORMATION: n = a, c, g or t
<220> FEATURE:
<221> NAME/KEY: unsure
<222> LOCATION: 279..279
<223> OTHER INFORMATION: n = a, c, g or t
<220> FEATURE:
<221> NAME/KEY: unsure
<222> LOCATION: 282..282
<223> OTHER INFORMATION: n = a, c, g or t
<220> FEATURE:
<221> NAME/KEY: unsure
<222> LOCATION: 294..294
<223> OTHER INFORMATION: n = a, c, g or t

<400> SEQUENCE: 26
caaaacagcc taactgccaa gactacaatg atcatgccca gtgcactcca ggaaaaagga      60
gtgacaacaa gcctccagat tagtggggac cattctatca atgccactca acccagtaag     120
ccatatgcag agccagtcag gtcagtgaga gaggcatctg agagacggtc ttcagattcc     180
taccctctcg ctcctgtcag agcacccaga acactgcagc ctcaacattg gacaacattt     240
tataaaccac atgnctccca atcatcagtt atcnagggng gnaatgaagg gagnaagc       298

<210> SEQ ID NO 27
<211> LENGTH: 429
<212> TYPE: DNA
<213> ORGANISM: Mus musculus

<400> SEQUENCE: 27
tcctcgacaa caaagtacat ttgcttttg accaagagca tgagtcagcg tcccaaaaga       60
tggaagatgt ctgtaaaagc cccaagctgc tgctgctgaa atccaatagg gcagcaaaca     120
gtgtgcagag acatactcca aggaccaaga tgagacctgt aagcttgcct gtagaccggc     180
tgcttcttct tgccagttct cctactgaga gaagcagcag ggatgtagga aacgtagact     240
cagacaagtt tggcaagaac cctgcctttg aaggactcca tagaaaggac aactcaaata     300
ctactcgctc caaagttaat ggctttgacc agcaaaatgt acagaaatcc tgggacacac     360
aatatgtacg gaacaatttt actgccaaga ctacgatgat tgttcccagt gcctaccctg     420
agaagggat                                                             429

<210> SEQ ID NO 28
<211> LENGTH: 386
<212> TYPE: DNA
<213> ORGANISM: Homo sapiens
<220> FEATURE:
<221> NAME/KEY: unsure
<222> LOCATION: 4..4
<223> OTHER INFORMATION: n = a, c, g or t
<220> FEATURE:
```

-continued

```
<221> NAME/KEY: unsure
<222> LOCATION: 5..5
<223> OTHER INFORMATION: n = a, c, g or t
<220> FEATURE:
<221> NAME/KEY: unsure
<222> LOCATION: 9..9
<223> OTHER INFORMATION: n = a, c, g or t
<220> FEATURE:
<221> NAME/KEY: unsure
<222> LOCATION: 10..10
<223> OTHER INFORMATION: n = a, c, g or t
<220> FEATURE:
<221> NAME/KEY: unsure
<222> LOCATION: 18..18
<223> OTHER INFORMATION: n = a, c, g or t
<220> FEATURE:
<221> NAME/KEY: unsure
<222> LOCATION: 29..29
<223> OTHER INFORMATION: n = a, c, g or t
<220> FEATURE:
<221> NAME/KEY: unsure
<222> LOCATION: 50..50
<223> OTHER INFORMATION: n = a, c, g or t
<220> FEATURE:
<221> NAME/KEY: unsure
<222> LOCATION: 55..55
<223> OTHER INFORMATION: n = a, c, g or t
<220> FEATURE:
<221> NAME/KEY: unsure
<222> LOCATION: 74..74
<223> OTHER INFORMATION: n = a, c, g or t
<220> FEATURE:
<221> NAME/KEY: unsure
<222> LOCATION: 77..77
<223> OTHER INFORMATION: n = a, c, g or t
<220> FEATURE:
<221> NAME/KEY: unsure
<222> LOCATION: 85..85
<223> OTHER INFORMATION: n = a, c, g or t
<220> FEATURE:
<221> NAME/KEY: unsure
<222> LOCATION: 107..107
<223> OTHER INFORMATION: n = a, c, g or t
<220> FEATURE:
<221> NAME/KEY: unsure
<222> LOCATION: 284..284
<223> OTHER INFORMATION: n = a, c, g or t
<220> FEATURE:
<221> NAME/KEY: unsure
<222> LOCATION: 321..321
<223> OTHER INFORMATION: n = a, c, g or t
<220> FEATURE:
<221> NAME/KEY: unsure
<222> LOCATION: 324..324
<223> OTHER INFORMATION: n = a, c, g or t
<220> FEATURE:
<221> NAME/KEY: unsure
<222> LOCATION: 327..327
<223> OTHER INFORMATION: n = a, c, g or t
<220> FEATURE:
<221> NAME/KEY: unsure
<222> LOCATION: 334..334
<223> OTHER INFORMATION: n = a, c, g or t
<220> FEATURE:
<221> NAME/KEY: unsure
<222> LOCATION: 338..338
<223> OTHER INFORMATION: n = a, c, g or t
<220> FEATURE:
<221> NAME/KEY: unsure
<222> LOCATION: 343..343
<223> OTHER INFORMATION: n = a, c, g or t
<220> FEATURE:
<221> NAME/KEY: unsure
<222> LOCATION: 344..344
<223> OTHER INFORMATION: n = a, c, g or t
<220> FEATURE:
<221> NAME/KEY: unsure
<222> LOCATION: 357..357
<223> OTHER INFORMATION: n = a, c, g or t
```

-continued

```
<220> FEATURE:
<221> NAME/KEY: unsure
<222> LOCATION: 385..385
<223> OTHER INFORMATION: n = a, c, g or t

<400> SEQUENCE: 28
caanngcann atcaaatntt aacagtctnc atttccttat agtacatcbn aagcnggtag      60
tagatcatgc aganganaac aagangaact ccaaaaactb gggggtnata tttggaccca     120
agtctcatta ggccaaggcc cacaactgct cctatcacca tctcctccct tgcagagtat    180
tcaaatcaag cacgcttggt agagtttctc attacttact cacagaagat cttcgatggg   240
tccctacagc cacaagatgt tatgtgtagc ataggtgttg ttgntcaagg ctgttttcca   300
aagcctctgt tatcaccaga nganagngac attnacgntc atnngtcact atttttncttt  360 caaaggaaga tatccatact tcagng                                        386

<210> SEQ ID NO 29
<211> LENGTH: 365
<212> TYPE: DNA
<213> ORGANISM: Homo sapiens
<220> FEATURE:
<221> NAME/KEY: unsure
<222> LOCATION: 230..230
<223> OTHER INFORMATION: n = a, c, g or t
<220> FEATURE:
<221> NAME/KEY: unsure
<222> LOCATION: 287..287
<223> OTHER INFORMATION: n = a, c, g or t
<220> FEATURE:
<221> NAME/KEY: unsure
<222> LOCATION: 307..307
<223> OTHER INFORMATION: n = a, c, g or t
<220> FEATURE:
<221> NAME/KEY: unsure
<222> LOCATION: 334..334
<223> OTHER INFORMATION: n = a, c, g or t
<220> FEATURE:
<221> NAME/KEY: unsure
<222> LOCATION: 339..339
<223> OTHER INFORMATION: n = a, c, g or t
<220> FEATURE:
<221> NAME/KEY: unsure
<222> LOCATION: 360..360
<223> OTHER INFORMATION: n = a, c, g or t

<400> SEQUENCE: 29
aaaacagcct aactgccaag actacaatga tcatgcccag tgcactccag gaaaaaggag      60
tgacaacaag cctccagatt agtggggacc attctatcaa tgccactcaa cccagtaagc    120
catatgcaga gccagtcagg tcagtgagag aggcatctga gagacggtct tcagattcct    180
accctctcgc tcctgtcaga gcacccagga acactgcagc ctcaacattn ggacaacatt    240
ttattaaacc acatgcttcc cattcattca gtattcaggg ggggatnagg gagaagccag    300 ctttcanccct tcaggcaggc agtgccttct gggncaggnt tcacggtttc cccacggtcn   360
ttgtg                                                                 365

<210> SEQ ID NO 30
<211> LENGTH: 456
<212> TYPE: DNA
<213> ORGANISM: Mus musculus

<400> SEQUENCE: 30
aattcgtcga caagcaatca ggcacgatta gtagagttcc ttattactta ctcacagaag      60
atcttcgatg ggtccctcca gcctcaagct gttgttatat ctaacacagg tgctgtggca    120
```

```
ctcaggttga tcaaggctat cttccaaaac ctctgttatc accagatgag agagacacag    180
atcattctat gaaaccactc ttttttttctt caaaggaaga tatccgtagt tcagattgtg    240
agagcaaaag ttttgaatta actacatctt ttgaagaatc agaacgcaga caaaatgcat    300
tggggaaatg tgacgctcct ctcctcgaca acaaagtaca tttgctttttt gaccaagagc    360 atgagtcagc gtcccaaaag atggaagatg tctgtaaaag ccccaagctg ctgctgctga    420
aatccaatag ggcagcaaac agtgtgcaga ggacat    456
```

```
<210> SEQ ID NO 31
<211> LENGTH: 295
<212> TYPE: DNA
<213> ORGANISM: Mus musculus

<400> SEQUENCE: 31
aagccccaag ctgctgctgc tgaaatccaa tagggcagca acagtgtgc agagacatac     60 tccaaggacc aagatgagac ctgtaagctt ccctgtagac cggctgcttc ttcttgccag   120
ttctcctact gagagaagca gcagggatgt aggaaacgta gactcagaca agtttggcaa   180
gaaccctgcc tttgaaggac tccatagaaa ggacaactca aatactactc gctccaaagt   240
taatggcttt gaccagcaaa atgtacagaa atcctgggac acacaatatg tacgg         295
```

```
<210> SEQ ID NO 32
<211> LENGTH: 546
<212> TYPE: DNA
<213> ORGANISM: Mus musculus

<400> SEQUENCE: 32
ggactgagga gaaaacagca ttaccctcaa tagctgtacc tcctgtcctg gtgcatgctc     60
cccagatcca tgtgacaaaa tcagacccag actcagaggc cacattggct gtcctgtgca   120
gacaagtggt caacctaaag agagctctga ggagcctgcc ctgcctgagg ggactccaac   180
ttgccagaga ccacgactaa aacgaatgca gcaatttgaa gaccttgaag atgaaatccc   240
acagtttgtg taggattgtc aaaatttaga ttttttctgtt ttattttgtt ctgtggtgtc   300
attttgtgag agaatgtttg gacagggccc ttttgtatag gattgccaaa gctgtttgtc   360
agtgtggtgt ttgttgctca tgtgggatgg gagagtgtcc tgacaaggct ccgtttagcc   420
tcactggaat gatctttgaa gctgtaaaga aaaatgggtg ttttttgtgtt ttttagagtt   480 gatttttttcc tgaagaatga tccatttaaa tgcatcactg atacatgata caattttttag   540 cagtag                                                                 546
```

```
<210> SEQ ID NO 33
<211> LENGTH: 328
<212> TYPE: DNA
<213> ORGANISM: Homo sapiens
<220> FEATURE:
<221> NAME/KEY: unsure
<222> LOCATION: 157..157
<223> OTHER INFORMATION: n = a, c, g or t
<220> FEATURE:
<221> NAME/KEY: unsure
<222> LOCATION: 181..181
<223> OTHER INFORMATION: n = a, c, g or t
<220> FEATURE:
<221> NAME/KEY: unsure
<222> LOCATION: 218..218
<223> OTHER INFORMATION: n = a, c, g or t

<400> SEQUENCE: 33
gtagctgttc atgttgattt aaatgagtaa aaaatttgaa cttttaaatt caatatacac    60
```

```
ctttaatact gtgcaaatgt ttaactcctc cacataggta actgagaata ttattttgga    120
aaaaatatgt aagactcata ttgtcttgat agagtgntca tctctaactc attcaaactc    180
ncttattaac catgtgccac aaacttaaat agatttcngg cattttcaga caaagcacag    240
ttgcttctag accaagaggc tgaatcagca tcccaaaaga tagaagatgg taaaacccct    300
aagccacttt ctctgaaatc cgatagg                                        328
```

```
<210> SEQ ID NO 34
<211> LENGTH: 601
<212> TYPE: DNA
<213> ORGANISM: Mus musculus
<220> FEATURE:
<221> NAME/KEY: unsure
<222> LOCATION: 493..493
<223> OTHER INFORMATION: n = a, c, g or t
<220> FEATURE:
<221> NAME/KEY: unsure
<222> LOCATION: 535..535
<223> OTHER INFORMATION: n = a, c, g or t

<400> SEQUENCE: 34
gtaagtacat tgtagctgtc ttcagacaca ccagaagagg gagtcagatc ttgttacgga     60
tggttgtgag ccaccatgtg gttgctagga cttgaactct ggaccttcag aagagcagtc    120
gggtgctctt acccactaag ccatctcacc agcccgtgat atctttatat atgtgtgtgc    180
acacacatgt gcatgtgtgt tacttatata tgtatataaa ggggctctca agtactaccc    240
atgttctgcc tgttgagtta tcaagcatat taaggtgtca ttgttttttct taaagtacac    300 atatgcatgt atattcgcta tgtctgagat agttcaaaca tcatttcaat ctctcactga    360
agttcagtta gactaatatt tagttatgta cctggactta tagactctga atccagagat    420
ctagactcac tgcttcctcc agtgctctct gagtcactaa acattccgaa cttccaggat    480
cttacgaaag aangaccttt aaaaaaagag taattaaaaa cttgcctaca ctaancccat    540
ggactacccc aacttggaga accatcccag gtgagaggag caaacctctg gaccctatta    600
a                                                                    601
```

```
<210> SEQ ID NO 35
<211> LENGTH: 613
<212> TYPE: DNA
<213> ORGANISM: Mus musculus

<400> SEQUENCE: 35
gtaagtacat tgtagctgtc ttcagacaca ccagaagagg gagtcagatc ttgttacgga     60
tggttgtgag ccaccatgtg gttgctagga cttgaactct ggaccttcag aagagcagtc    120
gggtgctctt acccactaag ccatctcacc agcccgtgat atctttatat atgtgtgtgc    180
acacacatgt gcatgtgtgt tacttatata tgtatataaa ggggcttctc aagtactacc    240
catgttctgc ctgttgagtt atcaagcata ttaaggtgtc attgttttc tttaaagtac    300 acatatgcat gtatattcgc tatgtctgag atagttcaaa catcatttca atctcctcac    360
tgaatgttca gttagactta atatttagtt attgtacctg gacttataga ctctgaatcc    420
agagatctag actcactgct tcctccagtg ctctctgagt cactaaacat tccgaacttc    480
caggatctta cgaaagaagg gacctttaaa aaagagtaa ttaaaaactt gcctacacta    540
acccattgga ctaccccaac tggagaacca tcccatgtga gaggagcaaa cctcggaccc    600
tattaatgga tac                                                       613
```

<210> SEQ ID NO 36
<211> LENGTH: 536
<212> TYPE: DNA
<213> ORGANISM: Mus musculus

<400> SEQUENCE: 36

| ttcgtcgaca aggacaaaat cagacccaga ctcagaggcc acattggctg tcctgtgcag | 60 |
| acaagtggtc aacctaaaga gagctctgag gagcctgccc tgcctgagcg ggactccaac | 120 |
| ttgccagagc accacgacta aaacgaatgc agcaatttga agaccttgaa gatgaaatcc | 180 |
| cacagtttgt gtaggattgt caaaatttag attttttctgt tttattttgt tctgtggtgt | 240 |
| cattttgtga gagaatgttt ggacagggcc cttttgtata ggattgccaa agctgtttgt | 300 |
| cagtgtggtg tttgttgctc atgtgggacg ggagagtgtc ctgacaaggc tccgtttagc | 360 |
| ctcactggaa tgatctttga agctgtaaag aaaaatgggt gttttttgtgt ttttttagagt | 420 |
| tgatttttc ctgaagaatg atccatttaa atgcatcact gatacatgat acaattttta | 480 |
| gcagtaggtg caattgggga aaatcagctt tagtgtggag agtgagccca agtgca | 536 |

<210> SEQ ID NO 37
<211> LENGTH: 198
<212> TYPE: DNA
<213> ORGANISM: Homo sapiens

<400> SEQUENCE: 37

| cttgctgtat gtgaatccaa tgtgtcagag accaaggcta aaacgaatgc aacagtttga | 60 |
| agacctcgaa gatgaaattc acaatttgtg tagggatgtc aaatttcagg gttttttttgt | 120 |
| tgttgttgtg ttattttgtg gtattgtgct tgttttgtga cagaatgttt tgacagggcc | 180 |
| cctttttgtat aggactgc | 198 |

<210> SEQ ID NO 38
<211> LENGTH: 614
<212> TYPE: DNA
<213> ORGANISM: Mus musculus

<400> SEQUENCE: 38

| cctaccttac tttctcgaga aataggtaga cgtatatcga gtcactgcct acgtctccca | 60 |
| taaggaagtt tgtgaggcta tccagagagg ttaaaaaaaa gcacagaaat aaaaagaaat | 120 |
| tattatactt cttggtctct taccgtcaat ctatcgtcta taataaattg ttttaagaaa | 180 |
| cacgtaagaa tcccattaca caaaccacag gcacagctcc taagagctct ataaatactt | 240 |
| gcgatacagt caatagagca acacagaagg tagctcttgt cgagctgtga tggcatgtga | 300 |
| tactacctaa cagtttattt tccattatcc cgcgattcat gtaccgtaca tcctcactaa | 360 |
| ggcatcagga gcactaactt caacgagagt cttcacttac agtttccaaa ggtaaatgcc | 420 |
| aatgtttcaa tggaggaaaa gacttctcgg aatatatcgt ttttgttttc ttcataactt | 480 |
| ctgtaaagtt cacagctata agcaaagatc agttgcagta agtggaggga aaacacctt | 540 |
| taacaccaga tttataccaa gtcatttact tcttttaatc accatggctt caaggcacca | 600 |
| aggaggtaga ggac | 614 |

<210> SEQ ID NO 39
<211> LENGTH: 508
<212> TYPE: DNA
<213> ORGANISM: Mus musculus

<400> SEQUENCE: 39

```
gcaaggggcg caggcagagc gaggacccg   ctccttctct gctctggctg agtgctgtgt       60
gccctttgaa cctggccagc gctaccagga gtttgttcag gaagtggaca ctgtccacag       120
ctgctcaaac ccaccgactg cggcggctgc ggggcccagc caagtgcaga gaatgtgaag       180
ccttcatggt cagcgggaca gaatgtgaag agtgcttttt gacctgtcac aagcgctgcc       240
tggagaccct cctcatcctt tgtggacacc ggcggcttcc agcccggatg tccctctttg       300
gggttgactt cctacagctc cccagagatt tccctgagga ggttcccttt gtgattacca       360
gatgcacagc tgagatagag caccgtgccc tgggcttgca gggtatctat cgggtcagcg       420
ggtctcgggt acgtgtggag cggctgtgca ggcctttgag aatggccgag cactggtcga       480
gctgtccggg aactctcctc acgatatc                                         508
```

ISOLATED NUCLEIC ACID MOLECULES ENCODING PARG, A GTPASE ACTIVATING PROTEIN WHICH INTERACTS WITH PTPL1

This application is a continuation-in-part of U.S. application Ser. No. 08/805,583, filed Feb. 25, 1997.

FIELD OF THE INVENTION

This invention relates to nucleic acids and encoded polypeptides which interact with the PTPL1 phosphatase and which are GTPase activating proteins. The invention also relates to agents which bind the nucleic acids or polypeptides. The invention further relates to methods of using such nucleic acids and polypeptides in the treatment and/or diagnosis of disease.

BACKGROUND OF THE INVENTION

The Rho family of Ras-like GTPases, which includes Rho, Rac and Cdc42, control actin-based cytoskeletal rearrangements (reviewed in Hall, *Annu. Rev. Cell Biol.* 10:31–54, 1994; Zigmond, *Curr. Opin. Cell Biol.* 8:66–73, 1996). Rho regulates receptor-mediated assembly of focal adhesions and stress fibers (Ridley and Hall, *Cell* 70:389–399, 1992), while Rac regulates the formation of membrane ruffles (Ridley et al., *Cell* 70:401–410, 1992) and Cdc42 controls the formation of filopodia (Nobes and Hall, *Cell* 81:53–62, 1995). Rho proteins have also been shown to be important in the regulation of cell proliferation (reviewed in Symons, *Trends Biochem. Sci.* 21:178–181, 1996). As members of the Ras superfamily, Rho proteins function as molecular switches, having an active, GTP-bound form, and an inactive, GDP-bound form. The active, GTP-bound form, is negatively regulated by GTPase activating proteins (GAPs) which enhance the intrinsic GTPase activity of Rho proteins. A number of GAPs that are active on proteins of the Rho family have been identified (reviewed in Lamarche and Hall, *TIG* 10:436–440, 1994). These include p50RhoGAP (Lancaster et al., *J. Biol. Chem.* 269:1137–1142, 1994), Myr5 (Reinhard et al., *EMBO J.* 14:697–704, 1995), and p190 (Settleman et al., *Nature* 359:153–154, 1992) which are also active on Rac and Cdc42. Another GAP, p122-RhoGAP (Homma and Emori, *EMBO J.* 14:286–291, 1995) appears to be specific for Rho.

Intracellular protein tyrosine phosphatases (PTPs) are a diverse group of proteins involved in signal transduction (reviewed in Streuli, *Curr. Opin. Cell Biol.* 8:182–188, 1996). They contain a conserved PTP domain which specifically dephosphorylates tyrosine residues and, in addition, domains that regulate their subcellular localization and activity (reviewed in Mauro and Dixon, *Trends Biochem. Sci.* 19:151–155, 1994). For example, the SH2 domains of SHP-1 and SHP-2 enables these PTPs to localize to and interact with activated growth factor receptors (Mauro and Dixon, 1994). Correct localization of PTPs is of importance, since the PTP domains usually have broad substrate specificity.

PTPL1 (Saras et al., *J Biol. Chem.* 269:24082–24089, 1994) also called PTP-BAS (Maekawa et al., *FEBS Lett.* 337:200–206, 1994), hPTP1E (Banville et al., *J. Biol. Chem.* 269:22320–22327, 1994) and FAP-1 (Sato et al., *Science* 268:411–415, 1995), is a 250 kDa protein expressed in many tissues and cell lines. PTPL1 is fully described in PCT published application WO95/06735. It contains an N-terminal leucine zipper motif followed by a domain with homology to the Band 4.1 superfamily. Band 4.1 -like domains are found in proteins involved in the linkage of actin filaments to the plasma membrane (Arpin et al., *Curr. Opin. Cell Biol.* 6:136–141, 1994). Five PDZ domains [PDZ is derived from PSD-95 (Cho et al., *Neuron* 9:929–942, 1992), Dlg-A (Woods and Bryant, *Cell* 66:451–464, 1991) and ZO-1 (Itoh et al., *J. Cell. Biol.* 121:491–502, 1993), each of which contains three such domains] are present between the Band 4. 1-like domain and the C-terminal PTP domain. These domain structures of about 90 amino acid residues have also been called GLGF repeats or DHRs and are identified in a variety of proteins (Ponting and Phillips, *Trends Biochem. Sci.* 20:102–103, 1995). A PDZ domain of PTPL1 has been shown to interact with the C-terminal tail of the membrane receptor Fas (Sato et al., 1995) and PDZ domains of PSD-95 bind to the C-terminals of the NMDA-receptor and Shaker-type $K^+$ channels (Kim et al., *Nature* 378:85–88, 1995; Komau et al., *Science* 269:1737–1740, 1995). The crystal structures of two PDZ domains have recently been published (Doyle et al., *Cell* 85:1067–1076, 1996; Morais Cabral et al., *Nature* 382:649–652, 1996).

There exists a need to influence the receptor-mediated intracellular signal transduction pathways to treat disease. There also exists a need to identify the gene(s) responsible for increased or decreased signal transduction and to provide a genetic therapy for treating diseases resulting from aberrant signal transduction.

An object of the invention is to provide compounds that desirably influence the signal transduction by the Rho family of Ras-like GTPases.

Another object of the invention is to provide therapeutics for treating diseases resulting from aberrant signal transduction by the Rho family of Ras-like GTPases. Still another object of the invention is to provide diagnostics and research tools relating to PARG, PTPL1 and the Rho family of Ras-like GTPases. These and other objects will be described in greater detail below.

SUMMARY OF THE INVENTION

The invention provides isolated nucleic acid molecules, unique fragments of those molecules, expression vectors containing the foregoing, and host cells transfected with those molecules. The invention also provides isolated polypeptides and agents which bind such polypeptides, including antibodies. The foregoing can be used in the diagnosis or treatment of conditions characterized by the expression of a PARG nucleic acid or polypeptide. The invention also provides methods for identifying pharmacological agents useful in the diagnosis or treatment of such conditions. Here, we present the cDNA cloning of a PTPL1-associated RhoGAP, PARG, a 150 kDa protein that contains a GAP domain that displays strong activity towards Rho. Furthermore, the C-terminal tail of PARG specifically interacts with the fourth PDZ domain (PDZ4) of PTPL1.

According to one aspect of the invention, an isolated nucleic acid molecule is provided. The molecule hybridizes under stringent conditions to a molecule consisting of the nucleic acid sequence of SEQ ID NO:1. The isolated nucleic acid molecule codes for a GTPase activating polypeptide. The invention further embraces nucleic acid molecules that differ from the foregoing isolated nucleic acid molecules in codon sequence due to the degeneracy of the genetic code. The invention also embraces complements of the foregoing nucleic acids.

In preferred embodiments, the isolated nucleic acid molecule comprises a molecule consisting of the nucleic acid sequence of SEQ ID NO:1. More preferably, the isolated nucleic acid molecule comprises a molecule consisting of nucleotides 184–3966 of SEQ ID NO:1. Preferably the isolated nucleic acid comprises a molecule having a sequence which encodes amino acids 666–853 of SEQ ID NO:2, amino acids 613–652 of SEQ ID NO:2, and/or amino acids 193–509 of SEQ ID NO:2.

According to another aspect of the invention, an isolated nucleic acid molecule is provided. The isolated nucleic acid molecule comprises a molecule consisting of a unique fragment of nucleotides 184–3966 of SEQ ID NO:1 between 12 and 3781 nucleotides in length and complements thereof, provided that the isolated nucleic acid molecule excludes molecules consisting solely of nucleotide sequences selected from the group consisting of accession numbers T32345 (SEQ ID NO:3), Z28937 (SEQ ID NO:4), Z28520 (SEQ ID NO:5), AA431926 (SEQ ID NO:14), AA326126 (SEQ ID NO:15), AA342471 (SEQ ID NO:16), AA716829 (SEQ ID NO:17), Z43348 (SEQ ID NO:18), AA303722 (SEQ ID NO:19), T32495 (SEQ ID NO:20), AA330162 (SEQ ID NO:21), Z25350 (SEQ ID NO:22), AA794256 (SEQ ID NO:23), T32506 (SEQ ID NO:24), T32263 (SEQ ID NO:25), F06673 (SEQ ID NO:26), AA462548 (SEQ ID NO:27), X85558 (SEQ ID NO:28), R14952 (SEQ ID NO:29), AA870705 272799.1 (SEQ ID NO:30), AA120493 (SEQ ID NO:31), AA415591 (SEQ ID NO:32), AA131400 (SEQ ID NO:33), C76597 (SEQ ID NO:34), C76601 (SEQ ID NO:35), AA870475 (SEQ ID NO:36), AA234871 (SEQ ID NO:37), C77518 (SEQ ID NO:38), and AA672012 (SEQ ID NO:39). In one embodiment, the isolated nucleic acid molecule consists of between 12 and 32 contiguous nucleotides of SEQ ID NO:1, or complements of such nucleic acid molecules. In preferred embodiments, the unique fragment is at least 14, 15, 16, 17, 18, 20 or 22 contiguous nucleotides of the nucleic acid sequence of SEQ ID NO:1, or complements thereof.

According to another aspect of the invention, an isolated nucleic acid molecule which encodes a PDZ domain binding site is provided, comprising a sequence selected from the group consisting of SEQ ID NO:6, SEQ ID NO:8 and SEQ ID NO:10, or nucleic acid molecules that differ from the nucleic acid molecules of the group consisting of SEQ ID NO:6, SEQ ID NO:8 and SEQ ID NO:10 in codon sequence due to the degeneracy of the genetic code. Preferably the isolated nucleic acid consists of a molecule having a sequence selected from the group consisting of SEQ ID NO:6, SEQ ID NO:8 and SEQ ID NO:10.

According to another aspect of the invention, the invention involves expression vectors, and host cells transformed or transfected with such expression vectors, comprising the nucleic acid molecules described above.

According to another aspect of the invention, an isolated polypeptide is provided. The isolated polypeptide is encoded by the isolated nucleic acid molecule of claim 1, 2 or 14, and the polypeptide has GTPase activating activity. In preferred embodiments, the isolated polypeptide comprises a polypeptide having the sequence of amino acids 658–898 of SEQ ID NO:2.

According to a further aspect of the invention, an isolated polypeptide is provided. The isolated polypeptide comprises a polypeptide encoded by a nucleic acid which hybridizes under stringent conditions to nucleotides 2020–2139 of SEQ ID NO:1. In preferred embodiments, the isolated polypeptide comprises a polypeptide having the sequence of amino acids 613–652 of SEQ ID NO:2 is provided. The isolated polypeptide has a Cys-rich domain.

According to another aspect of the invention, an isolated polypeptide is provided. The isolated polypeptide comprises a polypeptide encoded by a nucleic acid which hybridizes under stringent conditions to nucleotides 760–1710 of SEQ ID NO:1. In preferred embodiments, the isolated polypeptide comprises a polypeptide having the sequence of amino acid 193–509 of SEQ ID NO:2 is provided. The isolated polypeptide is a ZPH domain polypeptide.

In other embodiments, the isolated polypeptide consists of a fragment or variant of the foregoing which retains the activity of the foregoing.

According to still another aspect of the invention, an isolated polypeptide is provided. The isolated polypeptide is encoded by a nucleic acid molecule having a sequence selected from the group consisting of SEQ ID NO:6, SEQ ID NO:8 and SEQ ID NO:10. The isolated polypeptide comprises a polypeptide selected from the group consisting of a polypeptide having the sequence of SEQ ID NO:7, a polypeptide having the sequence of SEQ ID NO:9, and a polypeptide having the sequence of SEQ ID NO:11.

According to another aspect of the invention, there are provided isolated polypeptides which selectively bind a PARG protein or fragment thereof. The isolated polypeptide in certain embodiments binds to a polypeptide comprising the sequence of amino acids 658–898 of SEQ ID NO:2, amino acids 613–652 of SEQ ID NO:2, SEQ ID NO:7, SEQ ID NO:9, SEQ ID NO:11 or amino acids 193–509 of SEQ ID NO:2. The isolated polypeptide preferably binds to a polypeptide consisting essentially of the sequence of amino acids 658–898 of SEQ ID NO:2, amino acids 613–652 of SEQ ID NO:2, SEQ ID NO:7, SEQ ID NO:9, SEQ ID NO:11 or amino acids 193–509 of SEQ ID NO:2. In preferred embodiments, isolated binding polypeptides include antibodies and fragments of antibodies (e.g., Fab, F(ab)$_2$, Fd and antibody fragments which include a CDR3 region which binds selectively to the PARG polypeptides of the invention).

The invention provides in another aspect an isolated complex of polypeptides. The isolated complex includes a PTPL1 polypeptide, such a polypeptide including the amino acid sequence of SEQ ID NO:12 bound to a polypeptide as claimed in claim 1. The isolated complex has both PTPL1 phosphatase activity and PARG GAP activity. Preferably the isolated complex consists essentially of the polypeptide of SEQ ID NO:12 and the polypeptide of SEQ ID NO:2.

According to still another aspect of the invention, methods for reducing Rho family GTPase signal transduction in a mammalian cell are provided. The methods involve administering to a mammalian cell an amount of an inhibitor of Rho family GTPase activity effective to reduce Rho family GTPase signal transduction in the mammalian cell. In certain embodiments, the inhibitor is an isolated PARG polypeptide, having Rho GAP activity, encoded by SEQ ID NO:1. In other embodiments, the inhibitor is an isolated complex of polypeptides comprising a polypeptide comprising the amino acid sequence of SEQ ID NO:12 and a polypeptide comprising the amino acid sequence of SEQ ID NO:2.

According to still another aspect of the invention, methods for reducing proliferation of a cancer cell are provided. The methods involve administering to a cancer cell an amount of a PARG polypeptide, comprising a polypeptide encoded by the nucleic acid of claim 1, effective to reduce proliferation of the cancer cell.

The invention in a further aspect provides methods for increasing Rho family GTPase signal transduction in a mammalian cell. A dominant negative variant of the polypeptide of SEQ ID NO:2 is administered to the mammalian cell in an amount effective to increase Rho family GTPase signal transduction. Preferably the dominant negative polypeptide includes an inactivated GTPase activating domain which contains a deletion or at least one inactivating point mutation.

According to a further aspect of the invention, methods for reducing binding of a protein which includes a PDZ4 domain to a protein which includes a PDZ4 domain binding site are provided. The methods involve contacting the protein which includes PDZ4 domain with an agent which binds to the PDZ4 domain for a time effective to reduce the binding of the protein which includes PDZ4 domain to the protein which includes PDZ4 domain binding site. In certain embodiments the agent is an isolated peptide and includes at its carboxyl terminus the amino acid sequence of SEQ ID NO:7. The isolated peptide can include conservative substitutions of the amino acid sequence of SEQ ID NO:7, excepting the terminal valine. In preferred embodiments the amino acid sequence of the peptide is selected from the group consisting of SEQ ID NO:7, SEQ ID NO:9 and SEQ ID NO:11. In other embodiments the agent is an antibody which binds to the PDZ4 domain, preferably a monoclonal antibody. In some embodiments, methods provide inhibiting binding of a protein which includes a PDZ4 domain and a protein which includes a PDZ4 domain binding site in a mammalian cell. Such methods involve contacting the mammalian cell with an agent which binds to the PDZ4 domain for a time effective to reduce the binding of the protein which includes PDZ4 domain to the protein which includes PDZ4 domain binding site.

The invention in another aspect provides methods of modulating mast cell secretion in a subject. The methods include administering to the subject in need of such treatment an amount of a modulator of PARG GTPase activating activity effective to modulate mast cell secretion in the subject.

The invention in still another aspect provides compositions comprising a PARG polypeptide which has GTPase activating activity, a complex of such a PARG polypeptide and PTPL1 phosphatase, or a peptide agent which binds to a PDZ4 domain and which includes the sequence of SEQ ID NO:7, and a pharmaceutically acceptable carrier.

The invention in a further aspect involves a method for decreasing PARG GTPase activating activity in a subject. An agent that selectively binds to an isolated nucleic acid molecule of the invention or an expression product thereof is administered to a subject in need of such treatment, in an amount effective to decrease PARG GTPase activating activity in the subject. Preferred agents are antisense nucleic acids, including modified nucleic acids, and polypeptides.

According to another aspect of the invention, methods are provided for identifying lead compounds for a pharmacological agent useful in the diagnosis or treatment of disease associated with PARG GTPase activating activity or with PARG binding to a protein containing a PDZ4 domain. The methods involve forming a mixture of a PARG polypeptide or fragment thereof containing a GTPase activating domain or a PDZ4 domain binding site, a protein which interacts with the foregoing GTPase activating domain or PDZ4 domain binding site, and a candidate pharmacological agent. The mixture is incubated under conditions which, in the absence of the candidate pharmacological agent, permit a first amount of specific activation of the GTPase by the PARG GTPase activating domain or permit a first amount of selective binding of the protein containing a PDZ4 domain by the PDZ4 domain binding site. A test amount of the specific activation of the GTPase by the PARG GTPase activating domain or the selective binding of the protein containing a PDZ4 domain by the PDZ4 domain binding site then is detected. Detection of an increase in the foregoing activities in the presence of the candidate pharmacological agent indicates that the candidate pharmacological agent is a lead compound for a pharmacological agent which increases specific activation of the GTPase by the PARG GTPase activating domain or selective binding of the protein containing a PDZ4 domain by the PDZ4 domain binding site. Detection of a decrease in the foregoing activities in the presence of the candidate pharmacological agent indicates that the candidate pharmacological agent is a lead compound for a pharmacological agent which decreases specific activation of the GTPase by the PARG GTPase activating domain or selective binding of the protein containing a PDZ4 domain by the PDZ4 domain binding site. Where the activity tested is specific activation of the GTPase, the protein which interacts with the GTPase activating domain preferably is Rho. Where the activity tested is selective binding of a PDZ4 domain, the protein which interacts with the PDZ4 domain binding site preferably is PTPL1.

These and other objects of the invention will be described in further detail in connection with the detailed description of the invention.

BRIEF DESCRIPTION OF THE DRAWINGS

FIGS. 3A–3C depict the structure of PARG protein. (A) Deduced amino acid sequence of PARG SEQ ID NO:2. (B) Comparison of amino acid sequences of ZPH regions found in PARG SEQ ID NO:2 and in the gene product of the *C. elegans* gene ZK669.1a SEQ ID NO:13. (C) Schematic diagram illustrating the domain structure of PARG and ZK669.1a.

FIGS. 5A–5D shows an analysis of the GAP activity of PARG. (A) Expression of the GAP domain of PARG as a GST fusion protein. Rho (B), Rae (C), and Cdc42 (D) loaded with $\gamma$-$^{32}$P-GTP were incubated with 1 nM (open circles), 20 nM (filled circles) of the GAP domain of PARG expressed as a GST fusion protein, or 1 00 nM GST (squares) as a control, for different time periods at 30° C.

BRIEF DESCRIPTION OF THE SEQUENCES

Figure 1A:
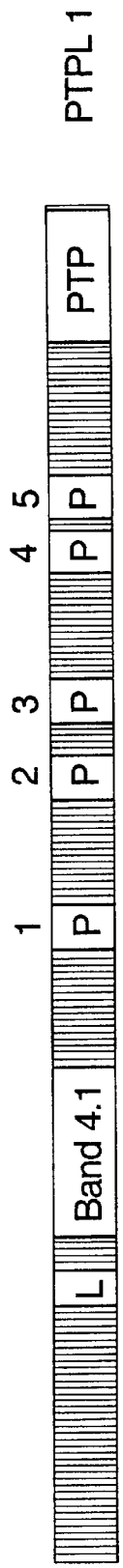
FIGS. 1A–1B are a representation of the production GST-PDZ fusion proteins. (A) Schematic illustration of the GST-PDZ fusion proteins showing the domain structure of PTPL1 and the design of PTPL1-derived GST-PDZ fusion proteins (B) Expression of GST-PDZ fusion proteins.

SEQ ID NO:1 is the nucleotide sequence of the PARG cDNA.

SEQ ID NO:2 is the amino acid sequence of the translation product of the PARG cDNA, including a RhoGAP domain at amino acids 666–853, a cysteine-rich domain at amino acids 613–652, a ZPH domain at amino acids 193–509 of SEQ ID NO:2, and a carboxyl-terminal PDZ domain binding site.

SEQ ID NO:3 is the nucleotide sequence of the expressed sequence tag identified by GenBank accession number T32345.

SEQ ID NO:4 is the nucleotide sequence of the expressed sequence tag identified by GenBank accession number Z28937.

SEQ ID NO:5 is the nucleotide sequence of the expressed sequence tag identified by GenBank accession number Z28520.

SEQ ID NO:6 is the nucleotide sequence encoding the PARG PDZ domain binding site which consists of 4 amino acids.

SEQ ID NO:7 is the amino acid sequence of the PARG PDZ domain binding site which consists of 4 amino acids.

SEQ ID NO:8 is the nucleotide sequence encoding the PARG PDZ domain binding site which consists of 5 amino acids.

SEQ ID NO:9 is the amino acid sequence of the PARG PDZ domain binding site which consists of 5 amino acids.

SEQ ID NO:10 is the nucleotide sequence encoding the PARG PDZ domain binding site which consists of 6 amino acids.

SEQ ID NO:11 is the amino acid sequence of the PARG PDZ domain binding site which consists of 6 amino acids.

SEQ ID NO:12 is the amino acid sequence of the PTPL1 phosphatase.

SEQ ID NO:13 is a portion of the amino acid sequence of the ZK669.1a protein (GenBank accession number Z37093)

Detailed Description of the Invention

The present invention in one aspect involves the cloning of a cDNA encoding a PARG GTPase activating protein. The sequence of the human gene is presented as SEQ ID NO:1, and the predicted amino acid sequence of this gene's protein product is presented as SEQ ID NO:2. Analysis of the sequence by comparison to nucleic acid and protein databases determined that PARG has several domains in addition to the GAP domain. These include a cysteine-rich domain located directly N-terminal of the GAP domain, a ZPII domain similar to the ZK669.1 gene product of *C. elegans* (Wilson et al., *Nature* 368: 32–38, 1994), and a PDZ domain binding site.

The GAP activity of PARG was determined as reported in Example 7 below. The GAP activity of this protein is strongest on Rho GTPase in vitro. GAP activities were also detected on Rac and Cdc42 in vitro. Because these activities on Rac and Cdc42 were observed at higher PARG concentrations than needed for Rho GAP activity, it is likely that Rho is the preferred in vivo target of PARG.

A cysteine-rich domain is located directly N-terminal of the GAP domain of PARG. This domain has been identified in various proteins including most PKC isoforms (which have two copies each of the domain), the protooncogene products Vav and Raf, diacylglycerol kinase and chimaerins (reviewed by Newton, *Curr. Biol.* 5: 973–976, 1995). The cysteine-rich domain has been shown to bind $Zn^{2+}$ (Ahmed et al., *Biochem J.* 280: 233–241, 1991), and the domains found in PKCs and in chimaerins also bind phorbol esters and diacylglycerol (Ahmed et al., 1991; Ono et al., *Proc. Natl. Acad Sci. USA* 86: 4868–4871, 1989). Generation of diacylglycerol or addition of phorbol ester increase the affinity of PKC molecules for membranes, and the resulting translocation of PKC from the cytosol to the plasma membrane is likely to involve interactions between the cysteine-rich domains and membrane phospholipids (Newton, 1995; Zhang et al., *Cell* 81: 917–924, 1995). The cysteine-rich domain of PARG may mediate regulatable binding to the membrane and could possibly also be involved in regulation of the GAP activity. Thus, a function of the cysteine-rich domain of PARG may be analogous to a function of n($\alpha$1)-chimaerin, a Rac-specific GAP, which contains a copy of a homologous cysteine-rich domain; it has been shown that phospholipids and phorbol esters regulate the GAP activity of n($\alpha$1)-chimaerin (Ahmed et al., *J. Biol. Chem.* 268: 10709–10712, 1993).

In the N-terminal part of PARG, a region of about 300 amino acid residues with similarity (27% identity) to the gene product of the *C. elegans* gene ZK669.1a was identified, and denoted ZPH region. The overall domain structure of the ZK669.1 a gene product is similar to PARG and it is possible that PARG is the human homolog of the *C. elegans* ZK669.1 a gene product. However, the RhoGAP domain and the cysteine-rich domain of the ZK669.1 a gene product is not significantly more similar to PARG (29% identity within the RhoGAP domains, 24% identity within the cysteine-rich domains) compared to other human proteins containing these domains (24–31% identity within the RhoGAP domains and 16–27% identity within the cysteine-rich domains).

PDZ domains have been identified in a diverse set of proteins (Ponting and Phillips, *Trends Biochem. Sci.* 20: 102–103, 1995). These proteins seem to be involved in signal transduction, and many of them, if not all, are found in structures at the plasma membrane. The size of the PDZ domain of about 90 amino acid residues, and its appearance in signal transduction proteins suggested that it, like SH2 and SH3 domains, can mediate direct interactions with other molecules. We have shown that PARG binds specificially to PDZ4 of PTPL1 and that the binding-site for binding to PDZ 4 resides in the four most C-terminal amino acid residues of PARG. PDZ domains can bind strongly to a short peptide of only four amino acid residues, and the carboxy-group and the side chain of the C-terminal valine residue is important for binding. The crystal structure of the third PDZ domain of PSD-95 binding to a peptide (Doyle et al., 1996; Morais Cabral et al., 1996) confirms these results and shows that the last four C-terminal amino acid residues of the peptide bind in a cleft of the domain with the C-terminal valine buried in a shallow pocket. Thus, the PDZ domain functions as a C-terminal peptide binding module. Because PDZ 4 binds to PARG, a complex between PTPL1, PARG, and Rho can be formed. Protein tyrosine kinases have been implicated to act upstream and downstream of Rho (Nobes and Hall, *J. Cell Sci.* 108:225–233, 1995; Ridley, *BioEssays* 16:321–327, 1994). Thus, PTPL1 can function as a negative regulator of kinases in the Rho signal pathway, and in complex with PARG, which inactivates Rho itself, it can be a powerful inhibitor of Rho signals.

The invention thus involves in one aspect PARG polypeptides, genes encoding those polypeptides, functional modifications and variants of the foregoing, useful fragments of the foregoing, as well as therapeutics relating thereto.

Homologs and alleles of the PARG nucleic acids of the invention can be identified by conventional techniques. Thus, an aspect of the invention is those nucleic acid sequences which code for PARG polypeptides and which hybridize to a nucleic acid molecule consisting of the coding region of SEQ ID NO:1, under stringent conditions. The term "stringent conditions" as used herein refers to parameters with which the art is familiar. Nucleic acid hybridization parameters may be found in references which compile such methods, e.g. *Molecular Cloning. A Laboratory Manual,* J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5× SSC, 0.02% Ficoll, 0.02% polyvinyl pyrolidone, 0.02% Bovine Serum Albumin, 2.5 mM NaH$_2$PO$_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2× SSC at room temperature and then at 0.1× SSC/0.1× SDS at temperatures up to 65° C.

There are other conditions, reagents, and so forth which can used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of PARG nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:1 and SEQ ID NO:2, respectively, in some instances will share at least 50% nucleotide identity and/or at least 65% amino acid identity and in still other instances will share at least 60% nucleotide identity and/or at least 75% amino acid identity. Watson-Crick complements of the foregoing nucleic acids also are embraced by the invention.

In screening for PARG proteins, a Southern blot may be performed using the foregoing conditions, together with a radioactive probe. After washing the membrane to which the DNA is finally transferred, the membrane can be placed against X-ray film to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating PARG polypeptide. Similarly, nucleotide sequence triplets which encode other amino acid residues include, but are not limited to,: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1 or complements of SEQ ID NO:1. A unique fragment is one that is a 'signature' for the larger nucleic acid. It, for example, is long enough to assure that its precise sequence is not found in molecules outside of the PARG nucleic acids defined above. Unique fragments can be used as probes in Southern blot assays to identify such nucleic acids, or can be used in amplification assays such as those employing PCR. As known to those skilled in the art, large probes such as 200, 250, 300, 400, 500 nucleotides or more are preferred for certain uses such as Southern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the PARG polypeptides, useful, for example, in the preparation of antibodies, in immunoassays, and as a competitive binding partner of the PTPL1 phosphatase and/or other polypeptides which bind to the PARG polypeptides, for example, in therapeutic applications. Unique fragments further can be used as antisense molecules to inhibit the expression of PARG nucleic acids and polypeptides, particularly for therapeutic purposes as described in greater detail below.

As will be recognized by those skilled in the art, the size of the unique fragment will depend upon its conservancy in the genetic code. Thus, some regions of SEQ ID NO:1 and its complement will require longer segments to be unique while others will require only short segments, typically between 12 and 32 nucleotides (e.g. 12, 13, 14, 15, 16, 17, 18, 19, 20, 21, 22, 23, 24, 25, 26, 27, 28, 29, 30, 31 and 32 bases long). Virtually any segment of the region of SEQ ID NO:1 beginning at nucleotide 184 and ending at nucleotide 3966, or its complement, that is 18 or more nucleotides in length will be unique. Those skilled in the art are well versed in methods for selecting such sequences, typically on the basis of the ability of the unique fragment to selectively distinguish the sequence of interest from non-PARG nucleic acids. A comparison of the sequence of the fragment to those on known data bases typically is all that is necessary, although in vitro confirmatory hybridization and sequencing analysis may be performed. Thus, for example, an examination of the nucleotide sequence databases indicates that at least a portion of the following sequences are identical to the PARG sequence, and thus nucleic acid molecules consisting solely of the following nucleotide sequences are not unique fragments of PARG: AA431926, AA326126, AA342471, AA716829, L49573, Z43348, AA303722, Z28520, T32495, AA330162, Z25350, AA794256, T32506, T32263, F06673, T32345, Z28937, AA462548, X85558, R14952, AA870705AA120493, AA415591, AA131400, C76597, C76601, AA870475, AA234871, C77518, and AA672012.

As mentioned above, the invention embraces antisense oligonucleotides that selectively bind to a nucleic acid molecule encoding a PARG polypeptide, to decrease GTPase activation by PARG or phosphatase binding by PARG. This is desirable in virtually any medical condition wherein a reduction in GTPase activating activity of PARG is desirable, including to reduce Rho family protein signal transduction, or wherein a reduction in phosphatase binding by PARG is desirable. Antisense molecules, in this manner, can be used to slow down or arrest the proliferation of cancer cells in vivo.

As used herein, the term "antisense oligonucleotide" or "antisense" describes an oligonucleotide that is an oligoribonucleotide, oligodeoxyribonucleotide, modified oligoribonucleotide, or modified oligodeoxyribonucleotide which hybridizes under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridization with the target gene or transcript. Those skilled in the art will recognize that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridize substantially more to the target sequence than to any other sequence in the target cell under physiological conditions. Based upon SEQ ID NO:1, or upon allelic or homologous genomic and/or cDNA sequences, one of skill in the art can easily choose and synthesize any of a number of appropriate antisense molecules for use in accordance with the present invention. In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840–844, 1996). Most preferably, the antisense oligonucleotides comprise a complementary sequence of 20–30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5):439–457, 1994) and at which proteins are not expected to bind. Finally, although, SEQ ID NO:1 discloses a cDNA sequence, one of ordinary skill in the art may easily derive the genomic DNA corresponding to the cDNA of SEQ ID NO:1. Thus, the present invention also provides for antisense oligonucleotides which are complementary to the genomic DNA corresponding to SEQ ID NO:1. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognized methods which may be carried out manually or by an automated synthesizer. They also may be produced recombinantly by vectors.

In preferred embodiments, however, the antisense oligonucleotides of the invention also may include "modified" oligonucleotides. That is, the oligonucleotides may be modified in a number of ways which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars which are covalently attached to low molecular weight organic groups other than a hydroxyl group at the 3' position and other than a phosphate group at the 5' position. Thus modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acids encoding PARG polypeptides, together with pharmaceutically acceptable carriers.

Antisense oligonucleotides may be administered as part of a pharmaceutical composition. Such a pharmaceutical composition may include the antisense oligonucleotides in combination with any standard physiologically and/or pharmaceutically acceptable carriers which are known in the art. The compositions should be sterile and contain a therapeutically effective amount of the antisense oligonucleotides in a unit of weight or volume suitable for administration to a patient. The term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual,* Second Edition, Cold Spring Harbor Laboratory Press, 1989. Cells are genetically engineered by the introduction into the cells of heterologous DNA (RNA) encoding PARG polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer,* 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

The invention also permits the construction of PARG gene "knock-outs" in cells and in animals, providing materials for studying certain aspects of GTPase activating activity and signal transduction.

The invention also provides isolated polypeptides, which include the polypeptide of SEQ ID NO:2 and unique fragments of SEQ ID NO:2, particularly amino acids 193–509, 613–652 and 658–898 of SEQ ID NO:2, as well as the carboxyl terminal 4, 5 or 6 amino acids of SEQ ID NO:2. Such polypeptides are useful, for example, alone or as fusion proteins to generate antibodies, as a components of an immunoassay.

A unique fragment of an PARG polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of amino acids 658–898 of SEQ ID NO:2, amino acid residues 613–652 of SEQ ID NO:2 and amino acid residues of 193–509 SEQ ID NO:2, will require longer segments to be unique while others will require only short segments, typically between 5 and 12 amino acids (e.g. 5, 6, 7, 8, 9, 10, 11 and 12 amino acids long). Virtually any segment of amino acids 658–898 of SEQ ID NO:2, amino acid residues 613–652 of SEQ ID NO:2 and amino acid residues of 193–509 SEQ ID NO:2, that is 10 or more amino acids in length will be unique.

Unique fragments of a polypeptide preferably are those fragments which retain a distinct functional capability of the polypeptide. Functional capabilities which can be retained in a unique fragment of a polypeptide include interaction with antibodies, interaction with other polypeptides (such as Rho) or fragments thereof, selective binding of nucleic acids or proteins (such as PTPL1), and enzymatic activity. Those skilled in the art are well versed in methods for selecting unique amino acid sequences, typically on the basis of the ability of the unique fragment to selectively distinguish the sequence of interest from non-family members. A comparison of the sequence of the fragment to those on known data bases typically is all that is necessary.

The invention embraces variants of the PARG polypeptides described above. As used herein, a "variant" of a PARG polypeptide is a polypeptide which contains one or more modifications to the primary amino acid sequence of a PARG polypeptide. Modifications which create a PARG variant can be made to a PARG polypeptide 1) to reduce or eliminate an activity of a PARG polypeptide, such as PTPL1 binding or GAP activity for Rho GTPase; 2) to enhance a property of a PARG polypeptide, such as protein stability in an expression system or the stability of protein-protein binding; or 3) to provide a novel activity or property to a PARG polypeptide, such as addition of an antigenic epitope or addition of a detectable moiety. Modifications to a PARG polypeptide are typically made to the nucleic acid which encodes the PARG polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the PARG amino acid sequence.

In general, variants include PARG polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a PARG polypeptide by eliminating proteolysis by proteases in an expression system (e.g., dibasic amino acid residues in yeast expression systems in which KEX2 protease activity is present).

Mutations of a nucleic acid which encode a PARG polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant PARG polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a PARG gene or cDNA clone to enhance expression of the polypeptide. The activity of variants of PARG polypeptides can be tested by cloning the gene encoding the variant PARG polypeptide into a bacterial or mammalian expression vector, introducing the vector into an appropriate host cell, expressing the variant PARG polypeptide, and testing for a functional capability of the PARG polypeptides as disclosed herein. For example, the variant PARG polypeptide can be tested for Rho GAP activity as disclosed in Example 7, or for PDZ binding as disclosed in other Examples herein. Preparation of other variant polypeptides may favor testing of other activities, as will be known to one of ordinary skill in the art.

The skilled artisan will also realize that conservative amino acid substitutions may be made in PARG polypeptides to provide functionally equivalent variants of the foregoing polypeptides, i.e, the variants retain the functional capabilities of the PARG polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning. A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the PARG polypeptides include conservative amino acid substitutions of SEQ ID NO:2, particularly conservative substitutions of amino acids other than 193–509, 613–652 or 658–898 of SEQ ID NO:2. However, conservative substitutions of amino acids 193–509, 613–652 or 658–898 of SEQ ID NO:2 can be made as well. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Changes to the carboxyl terminal valine of the PARG PDZ domain binding site are not preferred for retention of maximal binding activity.

Conservative amino-acid substitutions in the amino acid sequence of PARG polypeptides to produce functionally equivalent variants of PARG polypeptides typically are made by alteration of the nucleic acid encoding PARG polypeptides (SEQ ID NO:1). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by chemical synthesis of a gene encoding a PARG polypeptide. Where amino acid substitutions are made to a small unique fragment of a PARG polypeptide, such as a PDZ-domain binding site peptide, the substitutions can be made by directly synthesizing the peptide. The activity of functionally equivalent fragments of PARG polypeptides can be tested by cloning the gene encoding the altered PARG polypeptide into a bacterial or mammalian expression vector, introducing the vector into an appropriate host cell, expressing the altered PARG polypeptide, and testing for a functional capability of the PARG polypeptides as disclosed herein. Peptides which are chemically synthesized can be tested directly for function, e.g., for binding to a PDZ 4 domain of PTPL1.

The invention as described herein has a number of uses, some of which are described elsewhere herein. First, the invention permits isolation of the PARG protein molecule (SEQ ID NO:2). A variety of methodologies well-known to the skilled practitioner can be utilized to obtain isolated PARG molecules. The polypeptide may be purified from cells which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of mRNA in cell-free extracts such as the reticulocyte lysate system also may be used to produce polypeptide. Those skilled in the art also can readily follow known methods for isolating PARG polypeptides. These include, but are not limited to, immunochromotography, HPLC, size-exclusion chromatography, ion-exchange chromatography and immune-affinity chromatography.

The isolation of the PARG gene also makes it possible for the artisan to diagnose a disorder characterized by expression of PARG. These methods involve determining expression of the PARG gene, and/or PARG polypeptides derived therefrom. In the former situation, such determinations can be carried out via any standard nucleic acid determination assay, including the polymerase chain reaction as exemplified in the examples below, or assaying with labeled hybridization probes.

The invention also makes it possible isolate proteins having a PDZ4 domain by the binding of such proteins to the PDZ domain binding site disclosed herein. The identification of the PDZ domain binding site also permits one of skill in the art to block the binding of a protein having a PDZ4 domain, such as PTPL1, with a binding partner having a PDZ4 domain binding site, such as PARG. Binding of the proteins can be effected by introducing into a biological system in which the proteins bind (e.g., a cell) a polypeptide including a PDZ domain binding site in an amount sufficient to block the binding. The identification of the PDZ4 domain binding site in PARG also enables one of skill in the art to prepare modified proteins, using standard recombinant DNA techniques, which can bind to proteins containing a PDZ4 domain. For example, when one desires to target a certain protein to the inner membrane surface where proteins containing a PDZ domain, such as PTPL1, are localized, one can prepare a fusion polypeptide of the protein and the PDZ4 domain binding site. Preferably, the PDZ domain binding site is fused to the carboxy terminus of the protein. Additional uses are described further herein.

The invention further provides methods for reducing or increasing Rho family signal transduction in a cell. Such methods are useful in vitro for altering the Rho signal transduction, for example, in testing compounds for potential to block aberrant Rho signal transduction. In vivo, such methods are useful for modulating actin polymerization, cell proliferation and release of secretory granules from mast cells (see, e.g., Price et al., *Curr. Biol.* 5:68–73, 1995), e.g., to treat allergy. Increasing Rho signal transduction in a cell by, e.g., introducing a dominant negative PARG polypeptide in the cell, can be used to provide a model system for testing the effects of putative inhibitors of Rho signal transduction. Such methods also are useful in the treatment of conditions which result from excessive or deficient Rho signal transduction. Rho signal transduction can be measured by studying actin reorganization or by measuring the ratio of Rhobound GTP/GDP. Various modulators of PARG GTPase activating activity can be screened for effects on Rho signal transduction using the methods disclosed herein. The skilled artisan can first determine the modulation of a PARG activity, such as GTPase activating activity, and then apply such a modulator to a target cell or subject and assess the effect on the target cell or subject. For example, in screeing for modulators of PARG useful in the treatment of mast cell secretion, mast cells in culture can be contacted with PARG modulators and the increase or decrease of secretory granule release by the mast cells can be determined according to standard procedures. PARG activity modulators can be assessed for their effects on other Rho signal transduction downstream effects by similar methods in other cell types.

The invention also provides, in certain embodiments, "dominant negative" polypeptides derived from SEQ ID NO:2. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. For example, given the teachings contained herein of a PARG polypeptide, one of ordinary skill in the art can modify the sequence of the PARG polypeptide by site-specific mutagenesis, scanning mutagenesis, partial gene deletion or truncation, and the like. See, e.g., U.S. Pat. No. 5,580,723 and Sambrook et al., *Molecular Cloning.: A Laboratory Manual,* Second Edition, Cold Spring Harbor Laboratory Press, 1989. The skilled artisan then can test the population of mutagenized polypeptides for diminution in a selected activity (e.g., PARG GAP activity) and for retention of a desired activity (e.g., PARG binding to PTPL1). Other similar methods for creating and testing dominant negative variants of a protein will be apparent to one of ordinary skill in the art.

Dominant negative PARG proteins include variants in which a portion of the PDZ4 domain binding site has been mutated or deleted to reduce or eliminate PARG interaction with PTPL1. Other examples include partial deletion PARG variants which have the GAP domain deleted. Such variants retain the capability to bind PTPL1 but cannot enhance GTPase activity in Rho. A GAP-negative PARG variant does not, therefore, stimulate downstream signal transduction pathways such as the Rho pathway.

The invention also involves agents such as polypeptides which bind to PARG polypeptides and to complexes of PARG polypeptides and their phosphatase binding partners. Such binding agents can be used, for example, in screening assays to detect the presence or absence of PARG polypeptides and complexes of PARG polypeptides and their phosphatase binding partners and in purification protocols to isolate PARG polypeptides and complexes of PARG polypeptides and their phosphatase binding partners. Such agents also can be used to inhibit the native activity of the PARG polypeptides or their phosphatase binding partners, for example, by binding to such polypeptides, or their binding partners or both.

The invention, therefore, embraces peptide binding agents which, for example, can be antibodies or fragments of antibodies having the ability to selectively bind to PARG polypeptides. Antibodies include polyclonal and monoclonal antibodies, prepared according to conventional methodology.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pfc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining to the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for F(ab')$_2$, Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to PARG polypeptides, and complexes of both PARG polypeptides and their phosphatase binding partners. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the PARG polypeptide. This process can be repeated through several cycles of reselection of phage that bind to the PARG polypeptide. Repeated rounds lead to enrichment of phage bearing particular sequences. DNA sequence analysis can be conducted to identify the sequences of the expressed polypeptides. The minimal linear portion of the sequence that binds to the PARG polypeptide can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the PARG polypeptides. Thus, the PARG polypeptides of the invention, or a fragment thereof, can be used to screen peptide libraries, including phage display libraries, to identify and select peptide binding partners of the PARG polypeptides of the invention. Such molecules can be used, as described, for screening assays, for purification protocols, for interfering directly with the functioning of PARG and for other purposes that will be apparent to those of ordinary skill in the art.

A PARG polypeptide, or a fragment which contains the C-terminal PDZ4 domain binding site, also can be used to isolate their native binding partners, including, e.g., the PTPL1 phosphatase that complexes with PARG. Isolation of phosphatases may be performed according to well-known methods. For example, isolated PARG polypeptides can be attached to a substrate, and then a solution suspected of containing the phosphatase may be applied to the substrate. If the phosphatase binding partner for PARG polypeptides is present in the solution, then it will bind to the substrate-bound PARG polypeptide. The phosphatase then may be isolated. Other proteins which are binding partners for PARG, such as other proteins which contain PDZ4 domains may be isolated by similar methods without undue experimentation. Similarly, other proteins which bind PARG (e.g. Rho) can be isolated from biological samples and/or extracts by such methods.

Isolation of the PARG protein enables the skilled artisan to use the protein for isolation of molecules which bind to it. For example, isolated PARG can be used to isolate PTPL1 and other proteins which contain PDZ4 domains. The PARG or PDZ binding fragment can be immobilized on chromatographic media, such as polystyrene beads, or a filter, and the immobilized protein can be used to isolate proteins containing a PDZ4 domain from biological samples with no more than routine experimentation according to art-standard procedures for affinity chromatography. Such procedures are described in greater detail below.

It will also be recognized that the invention embraces the use of the PARG cDNA sequences in expression vectors, as well as to transfect host cells and cell lines, be these prokaryotic (e.g., E. coli), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells. The expression vectors require that the pertinent sequence, i.e., those nucleic acids described supra, be operably linked to a promoter.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp 1694–1712; incorporated by reference). Those of skill in the art can readily determine the various parameters and conditions for producing antibody aerosols without resort to undue experimentation. When using antisense preparations of the invention, slow intravenous administration is preferred.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The preparations of the invention are administered in effective amounts. An effective amount is that amount of a pharmaceutical preparation that alone, or together with further doses, produces the desired response. In the case of treating cancer, the desired response is inhibiting the progression of the cancer. This may involve only slowing the progression of the disease temporarily, although more preferably, it involves halting the progression of the disease permanently. This can be monitored by routine methods or can be monitored according to diagnostic methods of the invention discussed herein. Other therapeutic uses of PARG include the modulation of actin reorganization, and modulation of mast cell secretory granule release to treat allergic responses.

The invention also contemplates gene therapy. The procedure for performing ex vivo gene therapy is outlined in U.S. Pat. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention.

The invention further provides efficient methods of identifying pharmacological agents or lead compounds for agents active at the level of a PARG or PARG fragment modulatable cellular function. In particular, such functions include Rho signal transduction and formation of a PTPL1-PARG protein complex. Generally, the screening methods involve assaying for compounds which interfere with a PARG activity such as PARG-PTPL1 binding, etc. Such methods are adaptable to automated, high throughput screening of compounds. The target therapeutic indications for pharmacological agents detected by the screening methods are limited only in that the target cellular function be subject to modulation by alteration of the formation of a complex comprising a PARG polypeptide or fragment thereof and one or more natural PARG intracellular binding targets, such as PTPL1 or other protein including a PDZ 4 domain. Target indications include cellular processes modulated by Rho signal transduction following receptor-ligand binding and PTPL1-mediated phosphorylation.

A wide variety of assays for pharmacological agents are provided, including, labeled in vitro protein-protein binding assays, electrophoretic mobility shift assays, immunoassays, cell-based assays such as two- or three-hybrid screens, expression assays, etc. For example, three-hybrid screens are used to rapidly examine the effect of transfected nucleic acids on the intracellular binding of PARG or PARG fragments to specific intracellular targets. The transfected nucleic acids can encode, for example, combinatorial peptide libraries or antisense molecules. Convenient reagents for such assays, e.g., GAL4 fusion proteins, are known in the art. An exemplary cell-based assay involves transfecting a cell with a nucleic acid encoding a PTPL1-binding PARG polypeptide (e.g., including a PDZ domain binding site) fused to a GAL4 DNA binding domain and a nucleic acid encoding a PTPL1 PDZ 4 domain fused to a transcription activation domain such as VP16. The cell also contains a reporter gene operably linked to a gene expression regulatory region, such as one or more GAL4 binding sites. Activation of reporter gene transcription occurs when the PARG and PTPL1 PDZ 4 fusion polypeptides bind such that the GAL4 DNA binding domain and the VP16 transcriptional activation domain are brought into proximity to enable transcription of the reporter gene. Agents which modulate a PARG polypeptide mediated cell function are then detected through a change in the expression of reporter gene. Methods for determining changes in the expression of a reporter gene are known in the art.

PARG fragments used in the methods, when not produced by a transfected nucleic acid are added to an assay mixture as an isolated polypeptide. PARG polypeptides preferably are produced recombinantly, although such polypeptides may be isolated from biological extracts. Recombinantly produced PARG polypeptides include chimeric proteins comprising a fusion of a PARG protein with another polypeptide, e.g., a polypeptide capable of providing or enhancing protein-protein binding, sequence specific nucleic acid binding (such as GAL4), enhancing stability of the PARG polypeptide under assay conditions, or providing a detectable moiety, such as green fluorescent protein. A polypeptide fused to a PARG polypeptide or fragment may also provide means of readily detecting the fusion protein, e.g., by immunological recognition or by fluorescent labeling.

The assay mixture is comprised of a natural intracellular PARG binding target such as a Rho protein, PTPL1 protein or fragment thereof capable of binding to PARG. While natural PARG binding targets may be used, it is frequently preferred to use portions (e.g., peptides or nucleic acid fragments) or analogs (i.e., agents which mimic the PARG binding properties of the natural binding target for purposes of the assay) of the PARG binding target so long as the portion or analog provides binding affinity and avidity to the PARG fragment measurable in the assay.

The assay mixture also comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection. Candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease, inhibitors, nuclease inhibitors, antimicrobial agents, and the like may also be used.

The mixture of the foregoing assay materials is incubated under conditions whereby, but for the presence of the candidate pharmacological agent, the PARG polypeptide specifically binds the cellular binding target, a portion thereof or analog thereof. The order of addition of components, incubation temperature, time of incubation, and other perimeters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the presence or absence of specific binding between the PARG polypeptide and one or more binding targets is detected by any convenient method available to the user. For cell free binding type assays, a separation step is often used to separate bound from unbound components. The separation step may be accomplished in a variety of ways. Conveniently, at least one of the components is immobilized on a solid substrate, from which the unbound components may be easily separated. The solid substrate can be made of a wide variety of materials and in a wide variety of shapes, e.g., microtiter plate, microbead, dipstick, resin particle, etc. The substrate preferably is chosen to maximum signal to noise ratios, primarily to minimize background binding, as well as for ease of separation and cost.

Separation may be effected for example, by removing a bead or dipstick from a reservoir, emptying or diluting a reservoir such as a microtiter plate well, rinsing a bead, particle, chromotograpic column or filter with a wash solution or solvent. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

Detection may be effected in any convenient way for cell-based assays such as two- or three-hybrid screens. The transcript resulting from a reporter gene transcription assay of PARG polypeptide binding to a target molecule typically encodes a directly or indirectly detectable product, e.g., β-galactosidase activity, luciferase activity, and the like. For cell free binding assays, one of the components usually comprises, or is coupled to, a detectable label. A wide variety of labels can be used, such as those that provide direct detection (e.g., radioactivity, luminescence, optical or electron density, etc). or indirect detection (e.g., epitope tag such as the FLAG epitope, enzyme tag such as horseseradish peroxidase, etc.). The label may be bound to a PARG binding partner, or incorporated into the structure of the binding partner.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, strepavidin-biotin conjugates, etc. Methods for detecting the labels are well known in the art.

The invention provides PARG-specific binding agents, methods of identifying and making such agents, and their use in diagnosis, therapy and pharmaceutical development. For example, PARG-specific pharmacological agents are useful in a variety of diagnostic and therapeutic applications, especially where disease or disease prognosis is associated with improper utilization of a pathway involving PARG, e.g., Rho activation, PTPL1-PARG complex formation, etc. Novel PARG-specific binding agents include PARG-specific antibodies and other natural intracellular binding agents identified with assays such as two hybrid screens, and non-natural intracellular binding agents identified in screens of chemical libraries and the like.

In general, the specificity of PARG binding to a binding agent is shown by binding equilibrium constants. Targets which are capable of selectively binding a PARG polypeptide preferably have binding equilibrium constants of at least about $10^7 M^{-1}$, more preferably at least about $10^8 M^{-1}$, and most preferably at least about $10^9 M^{-1}$. The wide variety of cell based and cell free assays may be used to demonstrate PARG-specific binding. Cell based assays include one, two and three hybrid screens, assays in which PARG-mediated transcription is inhibited or increased, etc. Cell free assays include PARG-protein binding assays, immunoassays, etc. Other assays useful for screening agents which bind PARG polypeptides include fluorescence resonance energy transfer (FRET), and electrophoretic mobility shift analysis (EMSA).

Various techniques may be employed for introducing nucleic acids of the invention into cells, depending on whether the nucleic acids are introduced in vitro or in vivo in a host. Such techniques include transfection of nucleic acid-$CaPO_4$ precipitates, transfection of nucleic acids associated with DEAE, transfection with a retrovirus including the nucleic acid of interest, liposome mediated transfection, and the like. For certain uses, it is preferred to target the nucleic acid to particular cells. In such instances, a vehicle used for delivering a nucleic acid of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid delivery vehicle. For example, where liposomes are employed to deliver the nucleic acids of the invention, proteins which bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acids into cells, as is known by those skilled in the art. Such systems even permit oral delivery of nucleic acids.

EXAMPLES

Example 1
Production of PDZ Fusion Proteins

Figure 1B:
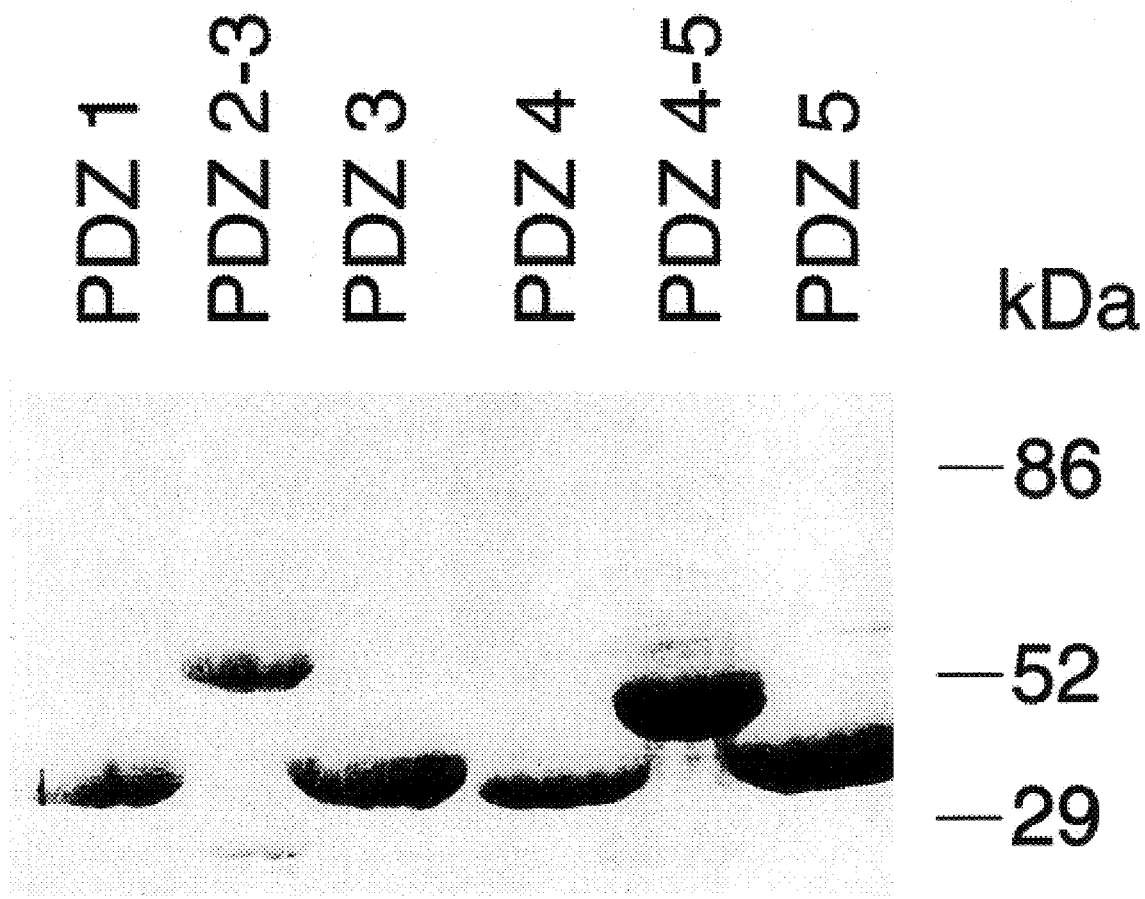

To identify proteins that bind to the PDZ domains of PTPL1, regions of PTPL1 cDNA corresponding to the various PDZ domains were produced by polymerase chain reaction and subcloned into the GST fusion protein expression vector pGEX1λT (Pharmacia): GST-PDZ 1. amino acid residues 1066–1166 of PTPL1; GST-PDZ 2-3. residues 1340–1579; GST-PDZ 3, residues 1469–1579; GST-PDZ 4, residues 1762–1864; GST-PDZ 4-5, residues 1762–1960 a GST-PDZ 5, residues 1856–1960 (FIG. 1A). Domains and motifs indicated in FIG. 1A are: L, leucine zipper motif; Band 4. 1, a domain of 300 amino acid residues with homology to the Band 4.1 superfamily; P, PDZ domain; PTP, protein tyrosine phosphatase catalytic domain; GST, glutathione S-transferase. The different expression vector constructs were transformed into *E. coli.* Glutathione S-transferase (GST) fusion proteins were produced and purified as described by Ridley and Hall (*Cell* 70: 389–399, 1992) and then subjected to sodium dodecyl sulfate (SDS)-gel electrophoresis. FIG. 1B shows that pure preparations of fusion proteins with to expected sizes were obtained.

Example 2
Identification of Proteins Which Bind to PDZ4

Figure 2:
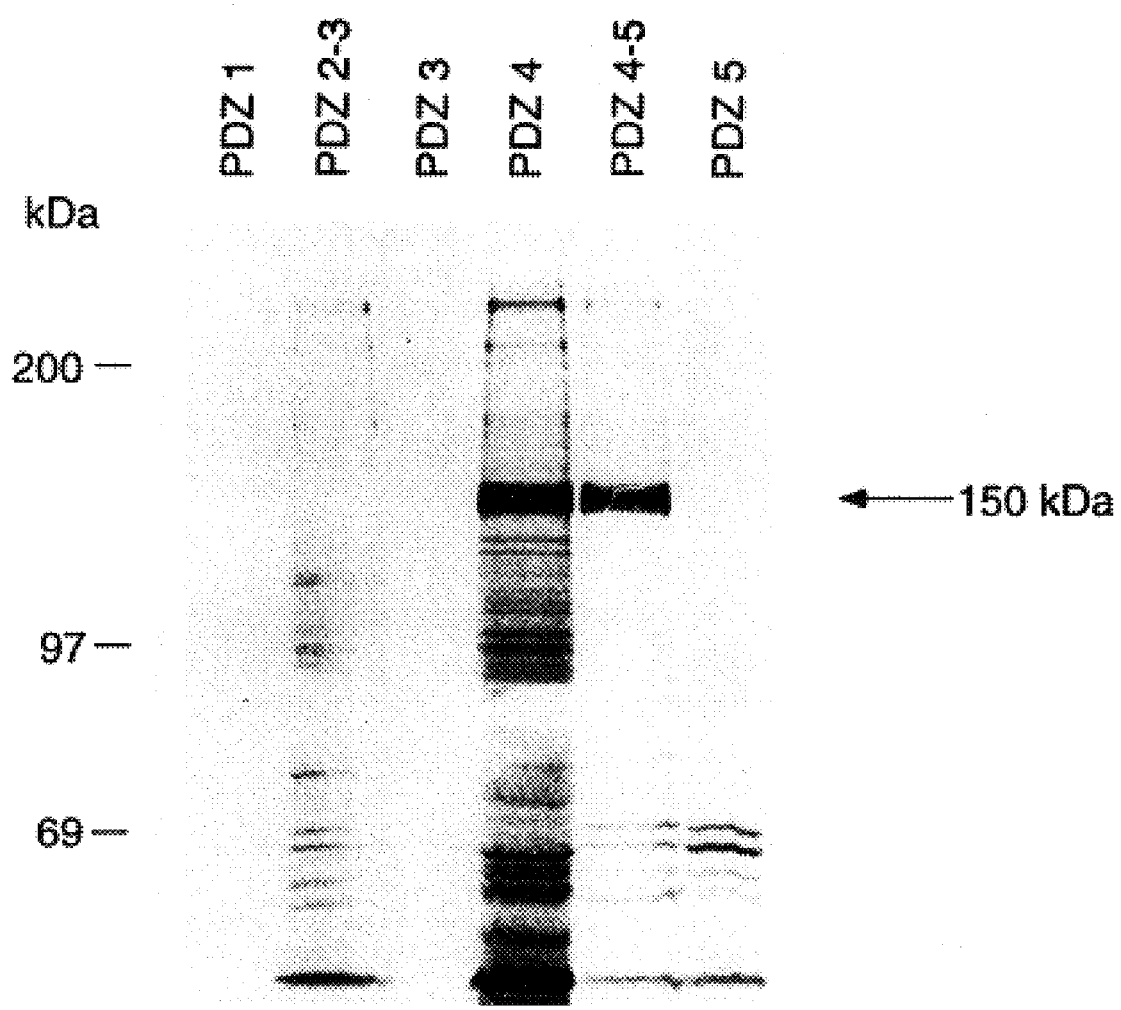
FIG. 2 shows the interaction of GST-PDZ fusion proteins with components in cell lysate.

PC-3 cells were obtained from American Type Culture Collection (Rockville, Md.) and cultured as described (Saras et al., 1994). Metabolic labeling of PC-3 cells was performed for 4 h in methionine- and cysteine-free MCDB 104 medium (Gibco/Life Technologies, Gaithersburg, Md.) with 150 Ci/ml of $^{35}$S-methionine and $^{35}$S-cysteine (in vivo labeling mix; Amersham, Arlington Heights, Ill.). After labeling, the cells were solubilized in buffer containing 20 mM Tris-HCI, pH 7.4,150 mM NaCl, 10 mM EDTA, 0.5% Triton X-100, 0.5% deoxycholate 1 mM dithiothreitol, 1.5% Trasylol (Bayer, Germany) and 1 mM phenylmethylsulfonyl fluoride (Sigma, St. Louis, Mo. ). After 15 min on ice, cell debris was removed by centrifugation. Samples (1 ml) were then incubated for 1.5 h at 4° C. with 10 μg of GST-PDZ fusion proteins bound to glutathione-Sepharose 4B beads (Pharmacia). The beads were pelleted and washed four times with solubilization buffer. The protein complexes were eluted by boiling for 5 min in SDS-sample buffer (100 mM Tris-4HCI, pH 8.8, 0.01% bromophenol blue, 36% glycerol, 4% SDS, 10 mM dithiothreitol) and analyzed by SDS-gel electrophoresis using 5–12% polyacrylamide gels (Blobel and Dobberstein, *J. Cell Biol.* 67: 835–851, 1975). The gel was fixed, incubated with Amplify (Amersham) for 20 min, dried and subjected to fluorography. A component of 150 kDa that bound to the fusion proteins GST-PDZ 4 and GST-PDZ-4-5 could be observed (FIG. 2); this component did not bind to GST fusion proteins containing PDZ domains 1, 2, 3 or 5 only, thus indicating that the 150 kDa component interacts specifically with PDZ 4 of PTPL1.

Example 3
Purification of 150 kDa Protein which binds to PDZ4

In order to characterize the 150 kDa component further, it was purified from PC-3 cells. Briefly, immobilized fusion protein GST-PDZ 4 was incubated with cell lysate from 1750 $cm^2$ of confluent PC-3 cells solubilized as described above. Samples (20 ml) were incubated for 1.5 h at 4° C. with 200 μg of GST-PDZ 4 fusion protein bound to glutathione-Sepharose 4B beads. The beads were washed and the bound proteins were eluted and subjected to SDS-get electrophoresis as described above.

After staining of the gel with Coomassie Brilliant Blue, the band that contained the 150 kDa component was excised and subjected to in-gel digestion using modified trypsin or EndoLysC protease. The band containing the 150 kDa component was transferred to Eppendorf tubes and subjected to in-gel digestion (Hellman et al., *Anal. Biochem.* 224: 451–455, 1995). In brief, the gel piece was washed with 0.2 M ammonium bicarbonate (for digestion with trypsin) or 0.5 M Tris-HCI pH 9.2 (for digestion with EndoLysC protease) and 50% acetonitrile, then dried completely. During rehydration, 0.5 μg of modified trypsin, sequence grade (Promega, Madison, Wis.) or 0.5 μg of EndoLysC (WAKO Chemicals, Richmond, Va.) was added and 0.2 M ammonium bicarbonate (for trypsin) or 0.1 M Tris-HCI pH 9.2 (for EndoLysC) was added in aliquots until the gel piece was immersed. After overnight incubation at 30° C., the supernatant was saved and combined with two further extractions from the gel piece. Generated peptides were isolated by reversed phase liquid chromatography using the SMART System (Pharmacia Biotech, Uppsala, Sweden). Peptides were sequenced on an Applied Biosystems (Foster City, Calif.) model 470A or 476A, following the manufacturers instructions.

Sequences were obtained from 10 peptides, and searches in different databases showed that none of these sequences were found in any known gene or protein, but the human Expressed Sequence Tags (ESTs) with GenBank accession numbers T32345, Z28937 and Z28520 (SEQ ID NOs:3, 4, 5), contained cDNA sequences corresponding to three of the obtained peptides. Oligonucleotides corresponding to the nucleotide sequences of the ESTs were designed and used as probes for Northern blots and screening of cDNA libraries.

Example 4
cDNA Cloning of PARG

The EST-derived oligonucleotides described above were used to screen different human cDNA libraries. Briefly, complementary and overlapping oligonucleotides corresponding to nucleotides 2–41 and 68–29 of an EST with the GenBank accession number Z28520 (SEQ ID NO:5) were made using a DNA synthesizer and labeled by a fill-in method (Sambrook et al., 1989) using the Klenow fragment of DNA polymerase I (Amersham) and α-$^{32}$P-dCTP (3000 Ci/mmol, Amersham). A λgt11 human skeletal muscle cDNA library (HL5002b; Clontech, Palo Alto, Calif.) was screened as described (Saras et al., 1994), using the $^{32}$P-labeled oligonucleotides as a probe. A positive clone was isolated, subcloned into pBluescript SK (Stratagene, La Jolla, Calif.) and thereafter sequenced.

Nucleotide sequencing revealed that the clone had a total length of 5237 bp with an open reading frame of 3783 bp, coding for a protein of 1261 amino acid residues. The open reading frame is flanked by a 5' untranslated sequence of 183 bp that contains an in frame stop codon at positions 166–168, and a 3' untranslated sequence of 1270 bp that has a poly(A) tail. The calculated molecular mass of the translated product is 142 kDa and the protein was, for reasons described below, denoted PARG. The amino acid sequence of PARG (SEQ ID NO:2) is shown in FIG. 3A; the nucleotide sequence (SEQ ID NO:1) has been deposited in the EMBL database.

Example 5
Structure of the PARG Protein

Figure 3C:
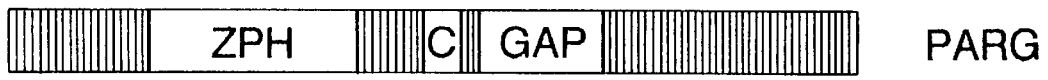
Figure 3C:

The amino acid sequence of PARG contained all peptide sequences obtained previously (FIG. 3A). In the deduced amino acid sequence of PARG no transmembrane domain or signal sequence for secretion were found, indicating that PARG is likely an intracellular protein. Three regions with homologies to other proteins could be identified: A GAP domain with similarity (23–33% amino acid sequence identity) to proteins of the RhoGAP family (Lamarche and Hall, 1994) is found at amino acid residues 666–853, a cysteine-rich region at amino acid residues 613–652 has homology to a regulatory, phorbol ester-, diacylglycerol- and Zn2+- binding domain of members of the protein kinase C (PKC) family (Newton, 1995), and a region at amino acid residues 193–509 has homology (27% identity) to the gene product of the C. elegans gene ZK669.1 a (EMBL accession numberr Z37093). FIG. 3B shows an alignment of the latter homology region, denoted ZPH region (for ZK667.1a-PARG homology). The alignment was done using the Clustal method (Higgins and Sharp, *CABIOS*5: 151–153, 1989), with some manual adjustment. Identical amino acid residues are boxed. Like PARG, the gene product of ZK669.1a contains in addition to the ZPH region, a cysteine-rich domain and a GAP domain (FIG. 3C). Domains and motifs indicated in FIG. 3C are: ZPH, ZK669.1a-PARG Homology region; C, cysteine-rich domain; GAP, RhoGAP domain.

Example 6
Expression of PARG mRNA

Northern blot analysis was performed to determine expression of the PARG mRNA. A Northern blot filter with mRNA from different human tissues was purchased from Clontech. Each lane contained 2 μg of polyadenylated RNA from the indicated tissues. The filter was hybridized with the $^{32}$P-labeled oligonucleotide probe described above, at 42° C. overnight in a hybridization solution containing 50% formamide, 5× SSC (1× SSC is 15 mM sodium citrate and 150 mM sodium chloride), 2× Denhardt's solution, 0.5% SDS, 50 mM sodium phosphate, pH 6.9, and 0.1 mg/ml salmon sperm DNA. The filter was washed two times in 0.5× SSC, 0.1% SDS at 55° C. for 15 min. After washing, the filter was exposed to Amersham Hyperfilm MP.

Figure 4:
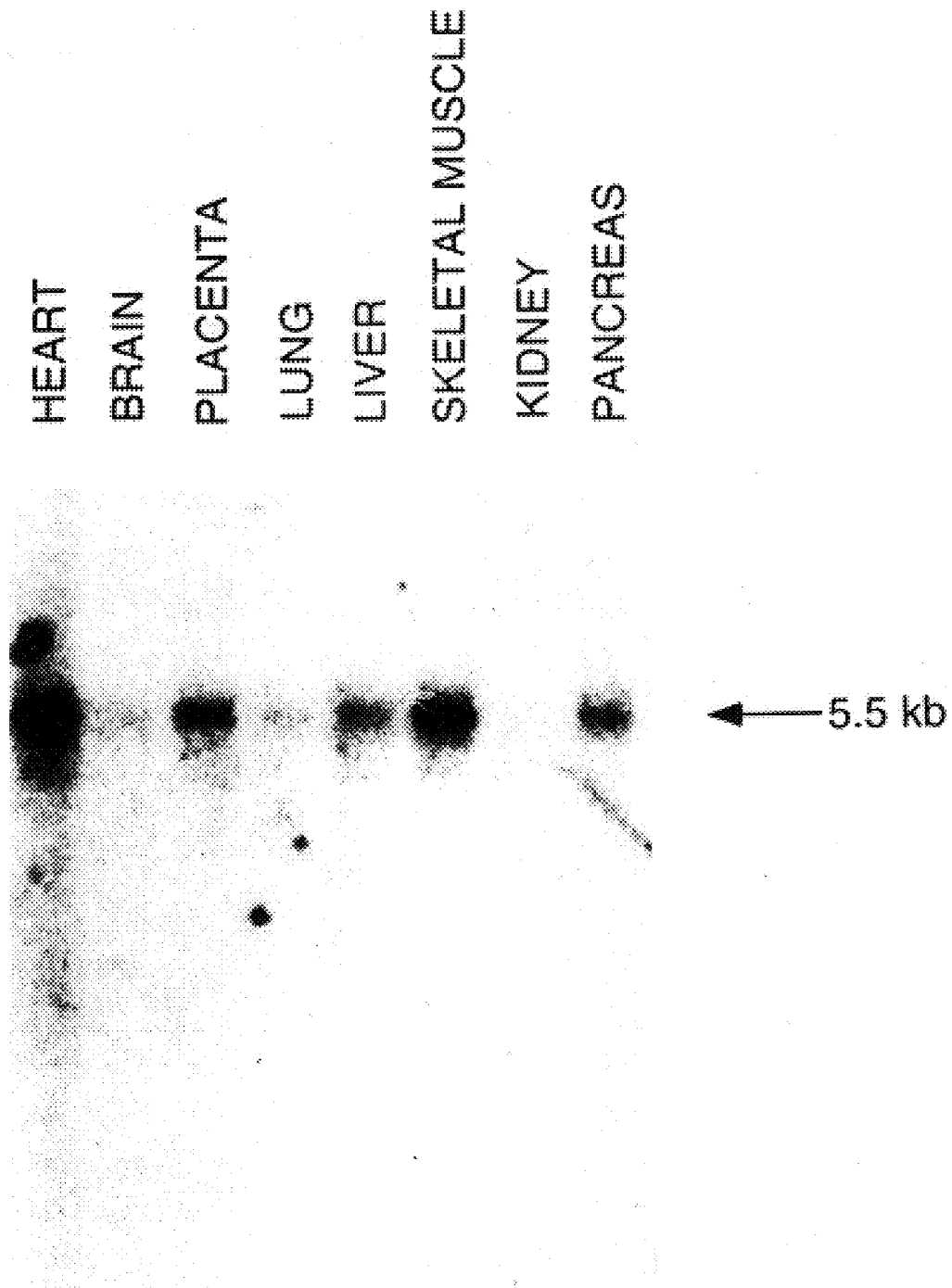
FIG. 4 shows Northern blot analysis of expression of PARG mRNA in different human tissues.

Northern blot analysis of mRNA from various human tissues showed that a single PARG transcript of 5.5 kb was found in all screened tissues (FIG. 4). The expression of PARG mRNA was high in skeletal muscle and heart and moderate in placenta, liver and pancreas. Low expression was observed in brain, lung and kidney. The size of the transcript suggested that the cDNA clone obtained was close to full length.

Example 7
GAP activity of PARG

Figure 5A:
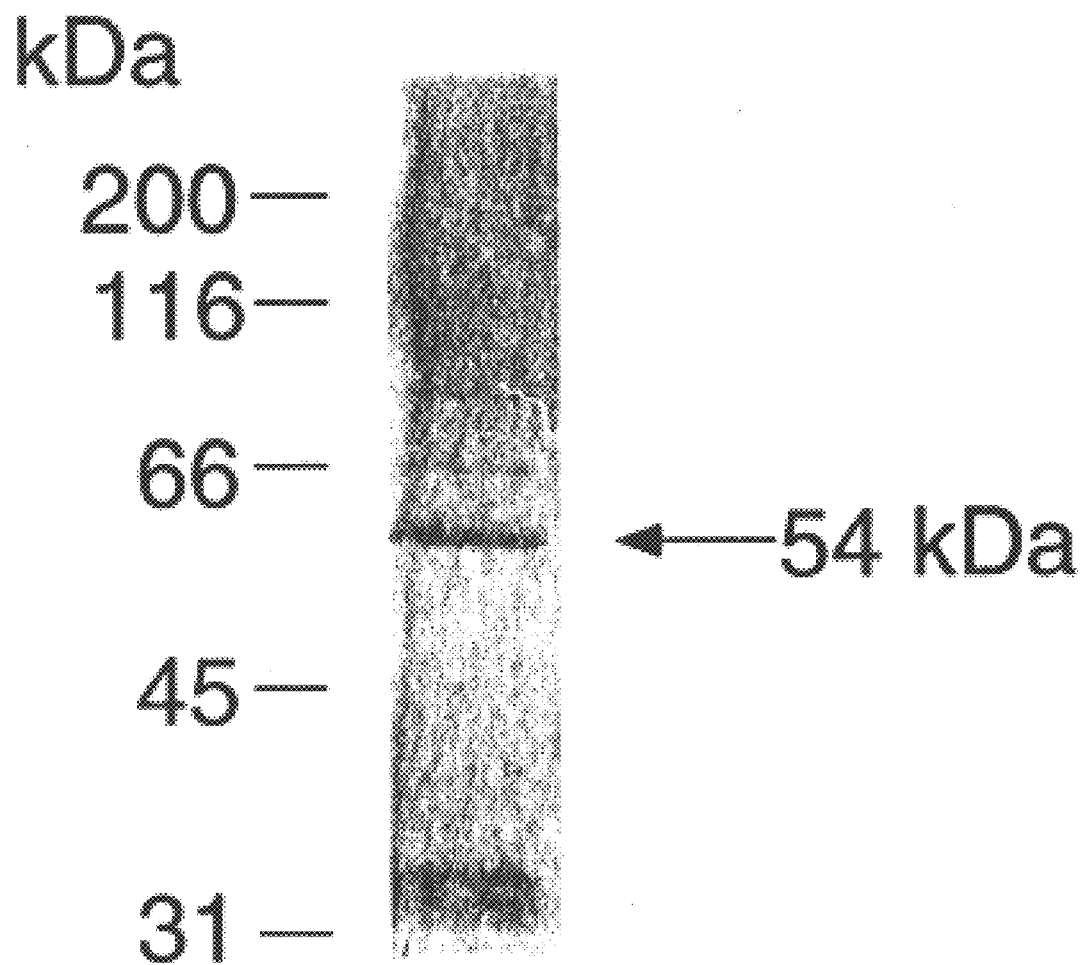

In order to determine the GAP activity of PARG on proteins of the Rho family, the GAP domain of PARG was produced as a GST fusion protein in *E. coli* (FIG. 5A). Briefly, a DNA fragment coding for the GAP domain, i.e., amino acid residues 658–898, of PARG was produced by polymerase chain reaction and subcloned into pGEX1λT and referred to as GST-GAP. pGEX2T-based expression vectors containing RhoA, Rac1 and Cdc42 (C25K isoform) cDNAs were obtained from Dr. A. Hall (MRC Laboratory for Molecular Cell Biology and Department of Biochemistry, University College London, UK). These different expression vector constructs were transformed into *E. coli*. The GST fusion proteins were produced and purified essentially as described above in Example 1. Recombinant Rho, Rae and Cdc42 proteins were subjected to thrombin cleavage (Ridley and Hall, 1992).

Recombinant Rho, Rae and Cdc42 were preloaded with γ-$^{32}$P-GTP and incubated for various time periods in the presence of the GST-GAP fusion protein or, as control, GST protein. Thereafter, the radioactivity bound to the GTPase was determined as a measurement of the GTP hydrolysis activity. Briefly, 200 nM aliquots of recombinant Rho, Rac and Cdc42 were incubated at 30° C. with 10 μCi γ-$^{32}$P-GTP in 20 mM Tris-HCI, pH 7.5, 25 mM NaCl, 4 mM EDTA, 0.1 mM dithiothreitol, and the nucleotide exchange was stopped after 10 min by the addition of 17 mM MgCl$_2$. Proteins (100 nM GST, 1 nM or 20 nM of GST-GAP fusion protein) were added to the reaction mixture and aliquots of 5 μl were withdrawn and collected on nitrocellulose filters (HA, Millipore, Bedford, Mass.) at 3 min intervals. The filters were washed with cold buffer (50 mM Tris-HCI pH 7.5, 50 mM NaCl, 5 mM MgCl$_2$), dried and subjected to scintillation counting. The amount of protein-bound radioactivity is expressed as the percentage of the total input.

The results show that the GAP domain of PARG, at the concentration of 1 nM, had a strong GAP activity on Rho (FIG. 5B). At this concentration, no GAP activity on Rac or Cdc42 was detected (FIG. 5C and 5D). However, at a concentration of 20 nM, the GST-GAP fusion protein was also active on Rac and Cdc42 (FIG. 5C and 5D). Thus, the results indicated that PARG has a functional GAP domain which, in vitro, is active on Rho, Rac and Cdc42, but with a clear preference for Rho. It is likely, therefore, that Rho is the physiological target of PARG. The name PARG is consequently derived from PTPL1 Associated RhoGAP.

Example 8
PDZ4 Binds to the C-terminal portion of PARG

It has been shown that PDZ domains interact with the C-terminal ends of short peptides and that a valine residue at the absolute C-terminal end is important for binding (Kim et al., 1995; Kornau et al., 1995; Saras et al., in preparation). Since PARG was identified through a specific interaction with PDZ 4 of PTPL1, and since it has a valine residue at the C-terminal end, we found it likely that the interaction is mediated via PDZ 4 and the C-terminal tail of PARG. To verify this possibility, peptides corresponding to the last 4, 5 or 6 C-terminal amino acid residues of PARG (PQFV, IPQFV and EIPQFV; SEQ ID Nos:7, 9 and 11) were synthesized in an Applied Biosystems 430A Peptide Synthesizer using t-butoxycarbonyl chemistry and purified by reversed phase high performance liquid chromatography. The peptides were coupled to Affigel 15 beads (Bio-Rad, Richmond, Calif.) via their N-terminal ends following the manufacturers instructions and incubated with GST-PDZ fusion proteins (50 nM) at 4° C. for 2 h in binding buffer (20 mM Tris-HCI, pH 7.4, 150 mM NaCl, 10 mM EDTA, 0.5% Triton X-100, 0.5% deoxycholate, 1 mM dithiothreitol). The beads were washed four times in binding buffer and bound fusion proteins were eluted by boiling for 5 min in SDS-sample buffer and subjected to SDS-gel electrophoresis using 11% polyacrylamide gels. After electrophoresis, the proteins were transferred to nitrocellulose membranes (Hybond C Extra; Amersham) and the membranes were incubated with a-GST antiserum (rabbit antiserum raised against recombinant GST expressed in bacteria). Bound antibodies were visualized by using enhanced chemiluminescence (ECL, Amersham), according to the manufacturer's instructions.

Figure 6:
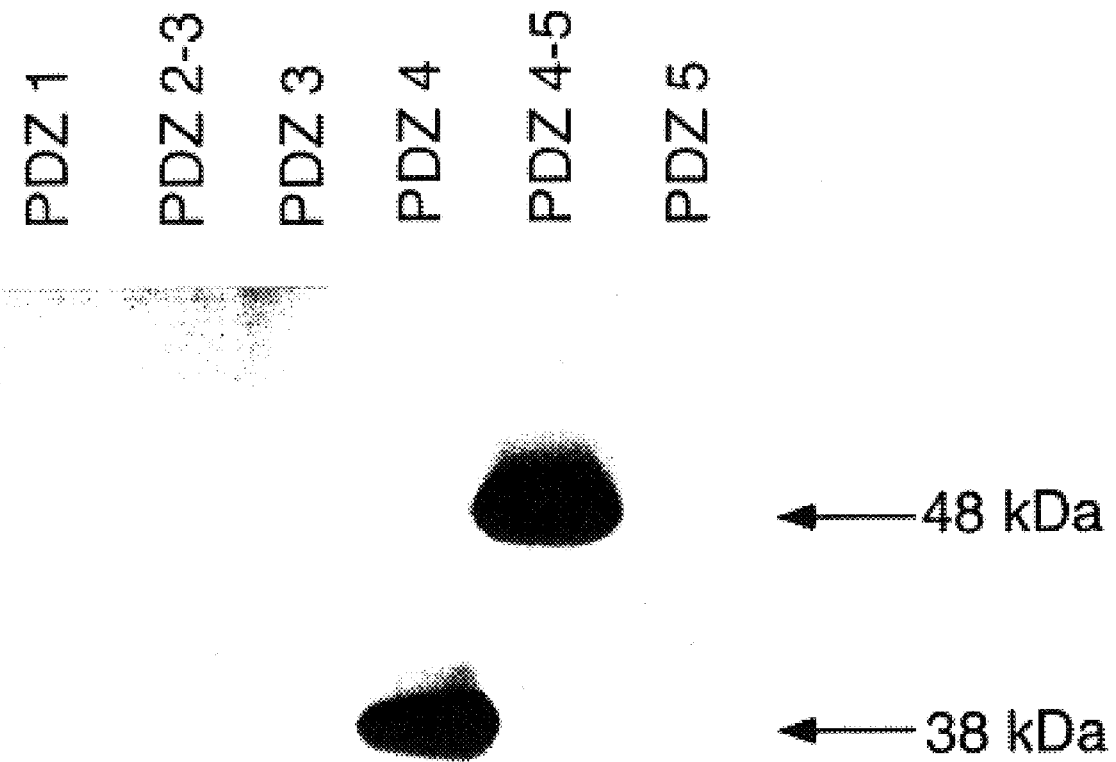
FIG. 6 shows binding of GST-PDZ fusion proteins to a C-terminal PARG peptide.

As shown in FIG. 6, the fusion proteins GST-PDZ 4 and GST-PDZ 4-5, but not GST fusion proteins containing PDZ 1, PDZ 2, PDZ 3 or PDZ 5 only, bound to the peptide corresponding to the last four amino acid residues of PARG. Similar results were obtained by using the longer peptides, indicating that a maximum of four amino acid residues at the C-terminal end of PARG is enough for a strong and specific interaction with PDZ 4 of PTPL1.

Equivalents

Those skilled in the art will recognize, or be able to ascertain using no more than routine experimentation, many equivalents to the specific embodiments of the invention described herein. Such equivalents are intended to be encompassed by the following claims.

A sequence listing is presented below and is followed by what is claimed:

What is claimed is:

1. An isolated nucleic acid molecule selected from the group consisting of
   (a) nucleic acid molecules which hybridize under stringent conditions to a molecule consisting of the nucleic acid sequence of SEQ ID NO:1 and which code for a GTPase-activating polypeptide, wherein the stringent conditions are selected from the group consisting of (1) hybridization at 65° C. in hybridization buffer (3.5× SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA), wherein SSC is 0.15M sodium chloride/0.15M sodium citrate, pH7, SDS is sodium dodecyl sulphate, and EDTA is ethylenediaminetetracetic acid; and (2) hybridization at 42° C. in a hybridization solution containing 50% formamide, 5× SSC (1× SSC is 15 mM sodium citrate and 150 mM sodium chloride), 2× Denhardt's solution 0.5% SDS, 50 mM sodium phosphate, pH 6.9, and 0.1 mg/ml salmon sperm DNA,
   (b) nucleic acid molecules that encode the GTPase-activating polypeptide encoded by the nucleic acid molecules of (a), and
   (c) full length complements of the nucleic acid molecules of (a) or (b).

2. The isolated nucleic acid molecule of claim 1, wherein the isolated nucleic acid molecule comprises nucleotides 184–3966 of SEQ ID NO:1.

3. The isolated nucleic acid molecule of claim 1, wherein the isolated nucleic acid molecule consists of SEQ ID NO:1.

4. The isolated nucleic acid molecule of claim 1, wherein the isolated nucleic acid molecule comprises a molecule having a sequence which encodes amino acids 658–898 of SEQ ID NO:2.

5. An isolated nucleic acid molecule selected from the group consisting of (a) a fragment of nucleotides 184–3966 of SEQ ID NO:1 between 12 and 3781 nucleotide length and (b) full length complements of "(a)", provided that the nucleic acid molecule excludes molecules consisting solely of nucleotide sequences selected from the group consisting of SEQ ID NOS:3–5 and 14–39.

6. The isolated nucleic acid molecule of claim 5, wherein the isolated nucleic acid molecule consists of at least 14 contiguous nucleotides.

7. The isolated nucleic acid molecule of claim 5, wherein the isolated nucleic acid molecule consists of at least 15 contiguous nucleotides.

8. An isolated nucleic acid molecule selected from the group consisting of
   (a) nucleic acid molecules having the sequence of SEQ ID NO:10;
   (b) nucleic acid molecules that encode the polypeptide encoded by the nucleic acid molecules of (a), and
   (c) full length complements of (a) and (b).

9. An expression vector comprising the isolated nucleic acid molecule of claim 1, operably linked to a promoter.

10. A host cell transformed or transfected with the expression vector of claim 9.

11. The isolated nucleic acid molecule of claim 5, wherein the isolated nucleic acid molecule consists of at least 16 contiguous nucleotides.

12. The isolated nucleic acid molecule of claim 5, wherein the isolated nucleic acid molecule consists of at least 17 contiguous nucleotides.

13. The isolated nucleic acid molecule of claim 5, wherein the isolated nucleic acid molecule consists of at least 18 contiguous nucleotides.

14. The isolated nucleic acid molecule of claim 5, wherein the isolated nucleic acid molecule consists of at least 20 contiguous nucleotides.

15. The isolated nucleic acid molecule of claim 5, wherein the isolated nucleic acid molecule consists of at least 22 contiguous nucleotides.

16. The isolated nucleic acid molecule of claim 5, wherein the isolated nucleic acid molecule consists of between 12 and 32 contiguous nucleotides.

17. An expression vector comprising the isolated nucleic acid molecule of claim 5 operably linked to a promoter.

18. An expression vector comprising the isolated nucleic acid molecule of claim 8 operably linked to a promoter.

19. A host cell transformed or transfected with the expression vector of claim 17.

20. A host cell transformed or transfected with the expression vector of claim 18.

21. A method for producing a nucleic acid molecule that encodes a GTPase-activating polypeptide, comprising
    expressing in an expression system the nucleic acid molecule of claim 1 operably linked to a promoter, and
    isolating the nucleic acid molecule encoding the GTPase-activating polypeptide from the expression system.

22. A method for making a nucleic acid molecule encoding a GTPase-activating polypeptide comprising
    culturing the host cell of claim 10, and
    isolating the nucleic acid molecule encoding the GTPase-activating polypeptide.

23. A method for producing a GTPase-activating polypeptide, comprising expressing in an expression system the nucleic acid molecule of claim 1 operably linked to a promoter, and isolating the GTPase-activating polypeptide from the expression system.

24. A method for making a GTPase-activating polypeptide comprising culturing the host cell of claim 10, and isolating the GTPase-activating polypeptide.

\* \* \* \* \*